US008048289B2

(12) United States Patent
Finkel

(10) Patent No.: US 8,048,289 B2
(45) Date of Patent: Nov. 1, 2011

(54) PARALLEL PATCH CLAMP SYSTEM

(75) Inventor: Alan S. Finkel, Sunnyvale, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 1321 days.

(21) Appl. No.: 11/222,576

(22) Filed: Sep. 9, 2005

(65) Prior Publication Data

US 2006/0194255 A1 Aug. 31, 2006

Related U.S. Application Data

(60) Provisional application No. 60/608,699, filed on Sep. 10, 2004, provisional application No. 60/614,361, filed on Sep. 28, 2004, provisional application No. 60/700,464, filed on Jul. 18, 2005.

(51) Int. Cl.
*G01N 33/487* (2006.01)

(52) U.S. Cl. ................. 205/777.5; 204/403.01

(58) Field of Classification Search .......... 204/400, 204/775, 403.01; 435/4; 205/777.5, 775
See application file for complete search history.

(56) References Cited

U.S. PATENT DOCUMENTS

| | | | |
|---|---|---|---|
| 4,055,799 A | 10/1977 | Coster et al. | |
| 6,699,697 B2 | 3/2004 | Klemic et al. | |
| 6,776,896 B1 | 8/2004 | Osipchuk | |
| 2002/0053915 A1 | 5/2002 | Weaver | |
| 2002/0063067 A1* | 5/2002 | Bech et al. ............... | 205/775 |
| 2002/0064841 A1* | 5/2002 | Klemic et al. ............ | 435/164 |
| 2002/0176801 A1 | 11/2002 | Giebeler et al. | |
| 2003/0070923 A1 | 4/2003 | Schroeder et al. | |
| 2003/0129581 A1 | 7/2003 | Owen et al. | |
| 2003/0146091 A1 | 8/2003 | Vogel et al. | |
| 2004/0055901 A1 | 3/2004 | Petersen et al. | |
| 2004/0146849 A1 | 7/2004 | Huang et al. | |
| 2004/0251145 A1 | 12/2004 | Robertson | |

FOREIGN PATENT DOCUMENTS

WO WO 99/66329 12/1999

OTHER PUBLICATIONS

Galli, Aurelio et al., "Sodium-dependent Norepinephrine-induced Currents in Norepinefrine-Transporter-Transfected HEK-293 Cells Blocked by Cocaine and Antidepressants." Journal of Experimental Biology 198, pp. 2197-2212 (1995).*
Hess, Peter et al. "Calcium Channel Selectivity for Divalent and Monovalent Cations." J. Gen. Physiol. vol. 88, pp. 293-319, Sep. 1986.*

(Continued)

*Primary Examiner* — Kaj K Olsen
(74) *Attorney, Agent, or Firm* — Michael J. Bastian; Bella Fishman

(57) ABSTRACT

A system for high-throughput analysis of membranous samples having ion channels including at least one membranous sample, a multi-compartment structure including an extracellular chamber, an opposing intracellular chamber and a partition separating the extracellular and intracellular chambers, the partition having a plurality of apertures fluidly and electrically coupling the extracellular and intracellular chambers, wherein at least one of the apertures is sealed by the at least one membranous sample, and another of the apertures is unsealed, a electric source configured to apply a current between the extracellular and intracellular chambers, wherein a portion of the current travels through the unsealed aperture, and a current sensor configured to measure the current between the extracellular and intracellular chambers. A method of using the system is also disclosed.

22 Claims, 17 Drawing Sheets

OTHER PUBLICATIONS

Anderson, C. R., et al., "Voltage clamp analysis of acetylcholine produced end-plate current fluctuations at frog neuromuscular junction" *J Physiol* (1973) 235:655-691.

Axon Instruments, Inc., "The axon guide for electrophysiology and biophysics laboratory techniques," (Jun. 1993).

Axon Instruments, Inc., "pCLAMP9 data acquisition and analysis for comprehensive electrophysiology user's guide," (Aug. 2003).

Chahine, M., et al., "Electrophysiological characteristics of cloned skeletal and cardiac muscle sodium channels" *Am J Physiol Heart Circ Physiol* (1996) 271(2):H498-H506.

Chandy, K. G., et al., "A family of three mouse potassium channel genes with intronless coding regions" *Science* (Feb. 1990) 247(4945):973-975.

Fertig, N., et al., "Microstructured glass chip for ion-channel electrophysiology" *Phys Rev E Stat Nonlin Soft Matter Phys* (2001) 64:040901.

Fertig, N., et al., "Whole cell patch clamp recording performed on a planar glass chip" *Biophys J* (Jun. 2002) 82(6):3056-3062.

Guthrie, H. et al., "A place for high throughput electrophysiology in cardiac safety: screening hERG cell lines and novel compounds with the IonWorks HT™ System" *Journal of Biomolecular Screening* (Dec. 2005)10(8):832-840.

Hamill, O. P. et al., "Improved patch-clamp techniques for high-resolution current recording from cells and cell-free membrane patches" *Pflugers Arch* (1981) 391:85-100.

Hille, "Ion Channels of Excitable Membranes" Third Edition (2001) 62, 87-92, 99, 101, 246, 393-396, 591, Sinauer Associates, Inc., Sunderland, Massachusetts U.S.A.

Kiss, L., et al., "High throughput ion-channel pharmacology: planar-array-based voltage clamp" *Assay and Drug Development Technologies* (Feb. 2003) 1(2):127-135.

Klemic, K. G., et al., "Micromolded PDMS planar electrode allows patch clamp electrical recordings from cells" *Biosens Bioelectron* (Jun. 2002) 17(6-7):597-604.

Molecular Devices, Corporation, "Leak current subtraction method for IonWorks™ HT" *Ionworks Ht Technical Notes #1*, (2003).

Nuss, H. B., et al., "Cardiac sodium channels (hH1) are intrinsically more sensitive to block by lidocaine than are skeletal muscle (μ 1) channels" *J Gen Physiol* (Dec. 1995) 106:1193-1209.

Pantoja, R. et al., "Bilayer reconstitution of voltage-dependent ion channels using a microfabricated silicon chip" *Biophys J* (Oct. 2001) 81:2389-2394.

Sakmann et al., "Single Channel Recording" (1995) 4-17, 21-28, 147-152, 158-159, 199, 208-210, 213-216, 248, 285-300, 330, 350-351, Plenum Press, New York, A Division of Plenum Publishing Corporation, New York, NY U.S.A.

Schmidt, C. et al., "A chip-based biosensor for the functional analysis of single ion channels" *Agnew Chem Int Ed* (2000) 39(17):3137-3140.

Schroeder, K., et al., "IonWorks™ Ht: A New high-throughput electrophysiology measurement platform" *J Biomol Screen* (2003) 8(1):50-64.

Sheets, M. F., et al., "Gating of skeletal and cardiac muscle sodium channels in mammalian cells" *J Physiol* (1999) 514(2):425-436.

Trapani, J. G., et al., "Control of ion channel expression for patch clamp recordings using an inducible expression system in mammalian cell lines" *BMC Neurosci* (Jul. 2003) 4(15):1-8.

Xu, J., Wang, et al., "Ion-channel assay technologies: quo vadis?" *Drug Discov Today* (2001) 6,:1278-1287.

Jackson, Meyer B., "Whole-cell voltage clamp recording," Current Protocols in Neuroscience, 1997, pp. 6.6.13-6.6.14, John Wiley & Sons, Inc.

* cited by examiner

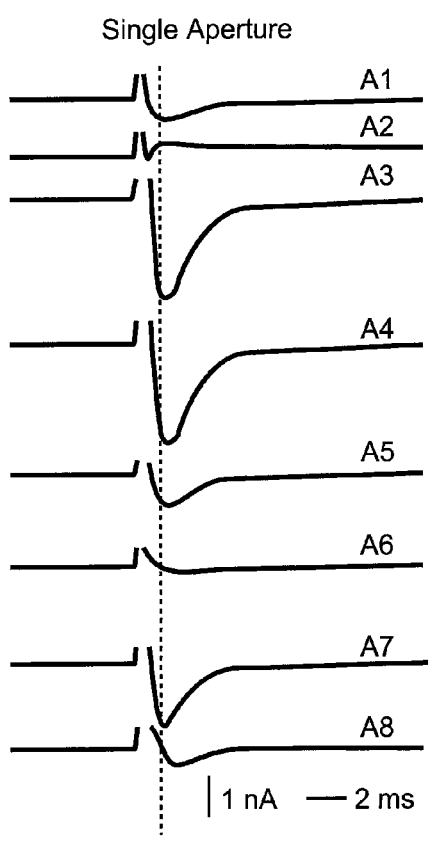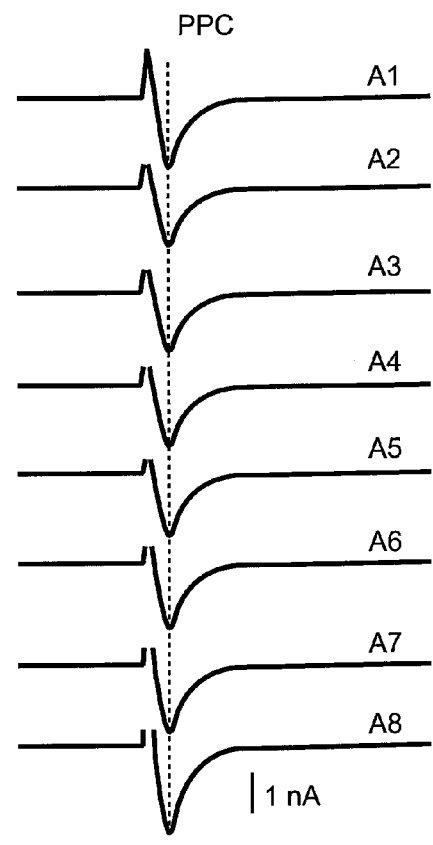
FIG. 13A
FIG. 13B

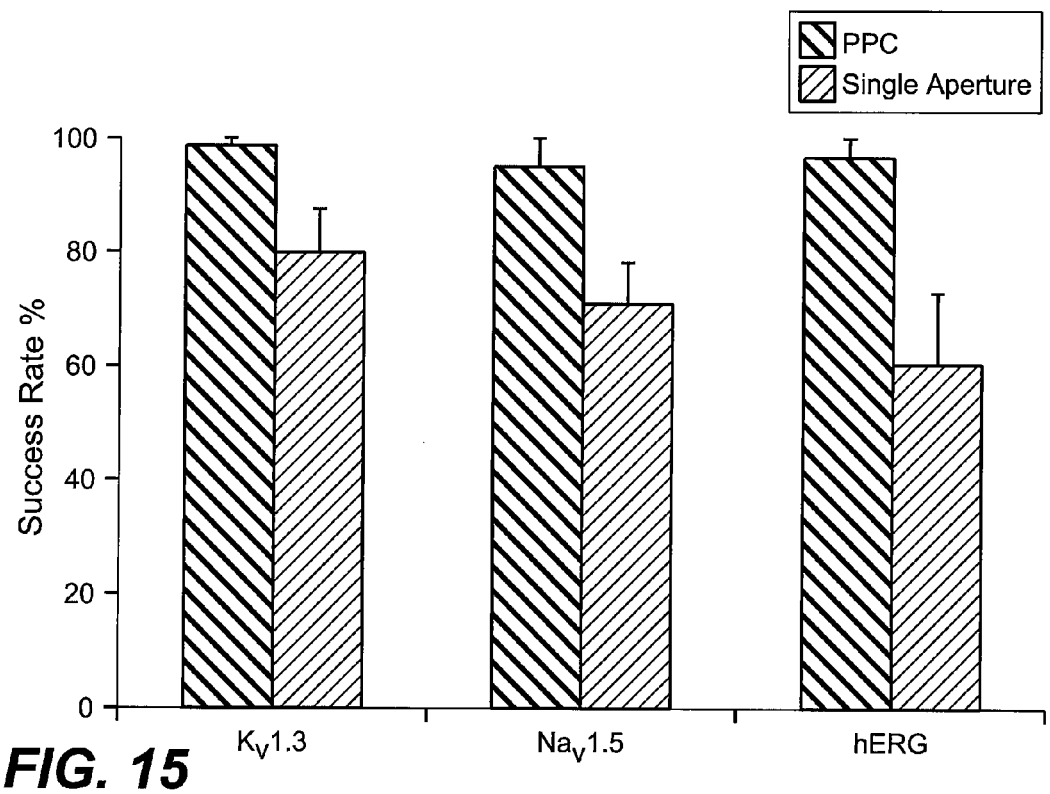
FIG. 15
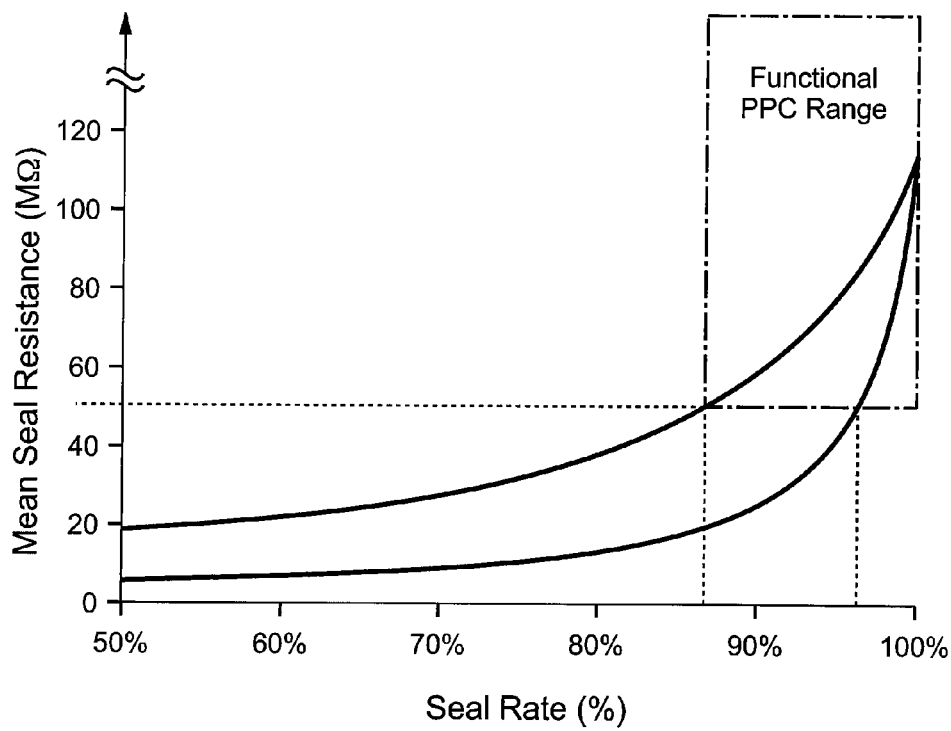
FIG. 17   Good Seal ≥ 120 MΩ, Remainder of seals = 3 MΩ
Good Seal ≥ 120 MΩ, Remainder of seals = 10 MΩ

PARALLEL PATCH CLAMP SYSTEM

CROSS-REFERENCES TO RELATED APPLICATIONS

This application claims priority to U.S. Provisional Patent Application No. 60/700,464 filed Jul. 18, 2005 and entitled POPULATION PATCH CLAMP IMPROVES DATA CONSISTENCY AND SUCCESS RATES IN THE MEASUREMENT OF IONIC CURRENTS, U.S. Provisional Patent Application No. 60/614,361 filed Sep. 28, 2004 and entitled ESTIMATION OF ELECTROPHYSIOLOGICAL PARAMETERS, and U.S. Provisional Patent Application No. 60/608,699 filed Sep. 10, 2004 and entitled POPULATION PATCH CLAMP SYSTEM, the entire contents of which applications is incorporated herein by this reference.

BACKGROUND OF THE INVENTION

1. Field of the Invention

The present invention relates to the field of electrophysiology, more specifically to the field of patch clamp electrophysiology, and most specifically to automated patch clamp electrophysiology instruments and systems, as well as methods for their use.

Electrophysiology includes, but is not limited to, the electrical properties of biological membranes, such as transmembrane potential(s) and the transmembrane flow of current through membrane-associated ion channels.

2. Description of Related Art

The basic concepts of patch clamp electrophysiology are known in the art. For reference, see *Single Channel Recording*, by Sakmann and Neher, all editions to date, *The Axon Guide* by Axon Instruments, Inc., and *Ion Channels of Excitable Membranes* by B. Hille, 3$^{rd}$ edition, all of which are incorporated herein by reference in their entirety for all purposes.

Electrophysiology may be studied using a variety of techniques. See, e.g., the above-mentioned *The Axon Guide*, *Single Channel Recording*, and *Ion Channels of Excitable Membranes*, all of which are incorporated herein by this reference. For example, the patch clamp technique may be used to study the electrical properties of membranes, including the flow of current through ion channels in the membranes. Typical patch clamp recording configurations are whole cell in single channel mode, both modes are known in the field. Typical whole cell recording requires gaining access to the cell interior usually facilitated by suction, zapping and antibiotic. FIG. 1 shows a fundamental equivalent electrical circuit, which models aspects of membrane electrical behavior. Here, the cell resistance R, also is known as the membrane resistance or the leak resistance. The pipette resistance $R_s$ often is referred to and is usually indistinguishable from the access, resistance or the series resistance.

Automated patch clamp devices to date voltage clamp a single cell per chamber, whether that chamber is a well in a cartridge, a flow through channel, or the inside or outside of a pipette. This may limit the throughput, limit the applications, and set a lower floor to the cost per data point, for reasons that will be described. Applicant also makes no representation that the following discussion is material to patentability, and the following discussion shall not be construed as an admission against interest in any manner.

Generally, there are two approaches used in today's automated patch clamps. These two approaches differ primarily in the methodology used to manage fluid exchange and to perform electrophysiological recording.

Approach I: Multiple Add, Reads, and Washes.

This approach is characterized by a single cell per well with fluidics capable of repetitively adding and removing fluids from each well independently. This approach utilizes fluidics to wash cells with buffer and add multiple compounds so that multiple data points can be acquired from each cell.

Typical devices are the PatchXpress® system from Molecular Devices Corporation, the Q-Patch from Sophion, and the Port-A-Patch from Nanion. These kinds of devices may be very flexible and can perform a wide variety of experiments, but their throughput is low. For example, the sixteen channel PatchXpress® 7000A can collect a maximum of about 240 data points per day (i.e., four data points per well, eight wells per SealChip® cartridge, and eight SealChip® cartridges per day, assuming 50% success rate on each SealChip cartridge, e.g., 50% of 16 wells per SealChip® cartridge=8 wells, experiment duration of 30-60 minutes).

Such systems can determine control responses on the same cell to which the test compound is applied, whether the applied compound modifies a voltage gated ion current (VGIC) or a ligand gated ion current (LGIC). By testing the viability of the cells and taking advantage of random access fluidics it is largely possible to guarantee that all compounds are tested, and other than statistical robustness there is no need to test a compound on more than one cell.

Approach II: Add and Read.

In an "add and read" system, no provision is made to wash the chamber with buffer or to replace or typically even top up the compounds; thus, only a single data point is acquired from each chamber.

This approach is embodied in the IonWorks® HT system from Molecular Devices Corporation. This system is limited to addition of solution and reading of the response (add and read). Compounds are added in groups, irrespective of the viability of the cells in the wells. The advantage of this system is that it is much simpler than a system that allows fluid exchange. The disadvantage is that since the typical rate of forming a successful whole cell recording configuration is in the vicinity of 60% to 70%, compounds have to be applied redundantly to guarantee that there is at least one successful recording of each compound. Usually the redundancy is four-fold, but eightfold or higher redundancy is required when the cells form the whole cell configurations at lower success rates. This redundancy both increases the cost per data point and decreases the throughput.

Like any measurement system, the add-and-read system can only work if a control measurement can be made to which the test compound response will be compared. In the case of VGICs, this is easy. First, the response to a series of voltage commands is measured before adding the test compound. This is the control response, representing 100%. Second, the response to the same series of voltage commands is measured after the test compound is added. Dividing this by the control response provides the percentage inhibition or activation.

It is not possible to make the control measurement in the case of LGICs because it would be necessary to add an agonist to determine the control response, then wash it out before adding the test compound (typically a mixture of test compound and agonist). This cannot be done in a conventional add-and-read system. One possible solution would be to measure the control response in one cell in a first well and add the test compound to a different cell in a second well. However, the variability in expression of ion channels in any given cell can range from zero to several times the average, thus the response to control compounds will have similar variability. The resulting errors involved in using a single cell as a control and a different cell for testing are unacceptable.

The throughput of add-and-read systems is high, relative to approach I. For example, in a typical 8-hour day, six to ten 384 well PatchPlate™ substrates will be processed, since the typical duration of an experiment is about 45-75 minutes. With the usual four-fold redundancy, 96 compounds will be delivered per 384 chamber PatchPlate™ substrate. Thus, the number of data points per day is nominally 600-1000.

For dose response applications in an add-and-read system, dose response curves are obtained by applying compounds at different doses to different groups of four chambers (assuming four-fold redundancy).

For either Approach I or Approach II, one of several compound delivery approaches can be utilized.

Fluidics I: Multiple Tips, Non-Random Access

In this approach, a multi-tip head is used to pick up many different compounds at once, to enhance or maximize throughput. In a basic implementation there is a one to one mapping between compound locations and dispense locations. Thus, if the cell at a particular patching location is unviable the compound will be dispensed at that location regardless. To guarantee that all compounds are tested, the compounds must be applied redundantly to multiple chambers, typically four or more chambers.

Fluidics II: Single Tip, Random Access

In this approach, a single-tip fluidics dispenser adds a compound to one chamber at a time. For example, the PatchXpress® system uses a Cavro® (Tecan) dispenser for this purpose. The advantage of this approach is that the software can choose any compound from any position. By analogy with computer memory this selection flexibility is known as "random access". The advantage of random access is that compounds do not have to be used in any particular order and all compounds can be accessed and applied irrespective of the success of the patching process in any given patch clamp chamber. The disadvantage of this approach is speed. There is simply a limit as to how fast a single pipetting head can pick up a disposable tip, aspirate compound, and dispense it in a chamber. A full cycle may take about fifteen seconds.

Fluidics III: Multiple Tips, Random Access

A modification of the Fluidics II approach is to use multiple tips with random access. This can be achieved through the use of multiple independent tip robots that are controlled through a central software application. Alternatively, approaches are currently available whereby the flow of solution in a multi-channel tip head can be controlled for each single tip. Additionally, robots exist that allow the control of inter-tip spacing in a multi-tip head, thus allowing for spatially and temporally controlled access to multiple wells from a multi-tip head.

In addition to commercial automated electrophysiology products currently available from companies such as Molecular Devices, Sophion, Nanion, etc., there are a number of patents and patent applications related to automated electrophysiology. Examples include U.S. patent application Ser. No. 09/900,627 (i.e., U.S. Patent Application Publication No. US 2002/0053915 A1), assigned to Bristol-Myers Squibb Company, and International Patent Publication No. WO 99/66329, assigned to CeNeS.

The existing devices and the existing literature indicate that there is a need in the field for a device and methods to automatically and accurately record electrophysiological signals with high throughput and high resolution for a variety of applications in a cost effective manner.

Other limitations of prior patch clamp techniques exist. During patch clamp recording, users may enable a variety of circuit compensation mechanisms, some of which may be found on commercial patch clamp amplifiers, including the Axopatch series of amplifiers by Molecular Devices Corporation. For example, users may nullify the electrode and/or whole cell capacitance, and activate series resistance compensation. Users also may enable passive leak subtraction.

During electrophysiological recording, it often is advantageous to estimate the electrical properties of the cell or preparation being analyzed. For example, users may want to estimate the whole cell capacitance or determine if the series resistance has changed during the course of the experiment. One approach that may be used is to apply a square voltage pulse to the cell being patch clamped, and then to analyze the current response of the cell. The current response to a square wave is a low-pass filtered, single- or multi-exponential decay, where the time constants of the waveform are a function of the resistance and capacitance of the cell and the instrumentation. The "Membrane Test" function in the industry standard software package pClamp (Molecular Devices Corporation) uses this approach to estimate various experimental parameters. See, e.g., *pCLAMP 9—DATA ACQUISITION AND ANALYSIS FOR COMPREHENSIVE ELECTROPHYSIOLOGY—User's Guide*, Axon Instruments, Inc. (August 2003). FIG. 2B shows an example of the data collected and estimated from the Membrane Test protocol in pClamp.

Unfortunately, in approaches such as that employed in Membrane Test, it may be very difficult accurately to curve fit the current response after electronic compensation has been enabled in the amplifier. For example, if whole-cell membrane capacitance compensation has been enabled, the passive membrane current response to a square voltage pulse will be significantly smaller or even zero, and thus accurate curve-fitting will be difficult or impossible, due to a lower signal-to-noise ratio.

Thus, there is a need for a system for estimating electrophysiological parameters during patch clamp recording, when compensation for at least some of these parameters has been enabled in the amplifier.

BRIEF SUMMARY OF THE INVENTION

Generally, the present invention provides for a system for high-throughput analysis of membranous samples having ion channels in which each well has more than one aperture, and in which analysis may be conducted irrespective of whether all apertures are perfectly sealed to a cell. Advantageously, the configuration of the present invention allows for increased success rate, increased throughput, increased data consistency, and reduced cost.

In summary, one aspect of the present invention is directed to a system for high-throughput analysis of membranous samples having ion channels, the system including: at least one membranous sample; a multi-compartment structure including an extracellular chamber, an opposing intracellular chamber and a partition separating the extracellular and intracellular chambers, the partition having a plurality of apertures fluidly and electrically coupling the extracellular and intracellular chambers, wherein at least one of the apertures is sealed by the at least one membranous sample, and another of the apertures is unsealed; and an electric source configured to apply a voltage and/or a current between the extracellular and intracellular chambers, wherein a portion of current travels through the unsealed aperture.

In one embodiment, the membranous sample may be selected from the group consisting of cells, vesicles, organelles, cell membrane fragments or synthetic membranes, which include an ion channel. The membranous sample may be substantially spherically shaped. The portion of the membranous sample outside of the one aperture of the partition may be substantially intact.

The multi-compartment structure includes a plurality of extracellular chambers and at least one opposing intracellular chamber, wherein the partition separates the extracellular chambers from the at least one intracellular chambers. The another of the apertures may be open. Each extracellular chamber may include at least 2, 10, 50, 64, 100 or 1000 apertures. The partition may be substantially planar. The apertures have a diameter in the range of approximately 0.5 µm to 5 µm.

The resistance associated with the unsealed aperture may be less than 50 Mohms, and the resistance associated with the at least one membranous sample sealed to the sealed aperture may be greater than 50 Mohms. The resistance associated with the unsealed aperture may be less than approximately 25%, 42%, 50% or 75% of the average resistance between the extracellular and intracellular chambers.

Optionally, the system may further include a current sensor configured to measure the current between the extracellular and intracellular chambers. The electric source and the current sensor may be respectively configured to begin applying and measuring the current across the extracellular and intracellular chambers before all apertures are sealed by respective membranous samples. The electric source may be an amplifier. The electric source may be a patch clamp amplifier.

The system may further include a fluidics system for adding fluids to the extracellular chamber, wherein the fluidics system may be configured to provide add, read and wash fluidics. The fluidics system may be configured to disperse a solution of membranous samples in suspension into the extracellular chamber. The at least one membranous samples may be sealed to the at least one aperture within five minutes of dispersion by the fluidics system. The at least one membranous samples may be sealed to the at least one aperture within 60 seconds of dispersion by the fluidics system. The at least one membranous sample has a low-resistance seal with the at least one aperture in the range of approximately 10 Mohm to 100 Mohm, and the electric source may be configured to voltage clamp the at least one membranous sample.

Optionally, the system may further include a first electrode in electrical contact with the extracellular chamber, and a second electrode in electrical contact with the intracellular chamber, wherein the first and second electrodes are electrically coupled with the electric source for applying the electrical voltage across the extracellular and intracellular chambers.

Another aspect of the present invention is directed to a method of high-throughput analysis of membranous samples having ion channels including: providing a system including a multi-compartment structure having an extracellular chamber, an opposing intracellular chamber and a partition separating the extracellular and intracellular chambers, the partition having a plurality of apertures fluidly and electrically coupling the extracellular and intracellular chambers, wherein the apertures are dimensioned and configured for electrically sealing a membranous sample; dispersing a plurality of membranous samples into the extracellular chamber such that the membranous samples seal at least one of the apertures; applying electrical voltage and/or current between the extracellular and intracellular chambers while another of the apertures is unsealed; and detecting a resulting current and/or voltage across the extracellular and intracellular chambers, wherein a portion of current travels though the unsealed aperture.

In one embodiment, the dispersing step may be accomplished by dispersing a solution of membranous samples in suspension into the extracellular chamber. The membranous samples may be selected from the group of cells, vesicles, organelles, cell membrane fragments or synthetic membranes, which samples include an ion channel. The membranous sample may be substantially spherically shaped. A portion of the membranous sample outside of the one aperture of the partition may be substantially intact. The membranous sample may have a low-resistance seal with the at least one sealed aperture that is at least approximately 10 Mohm, 100 Mohm, or 1000 Mohm.

The dispersing step may be accomplished by at least two membranous samples sealing at least two respective apertures, the method further including the step of summing the resulting current and/or voltage based on the two sealed membranous samples. Also, the dispersing step may be accomplished by at least two membranous samples sealing at least two respective apertures, the method further including the step of averaging the resulting current and/or voltage based on the two sealed membranous samples. Alternatively, the dispersing step may be accomplished by at least n membranous samples sealing n respective apertures, the method further including the step of averaging the resulting current and/or voltage based on the n sealed membranous samples.

The applying step may further include voltage clamping the one membranous sample. The applying and detecting steps may be initiated before the membranous sample seals to the at least one aperture.

The method further including the step of recording the current. The recording step may be begun within approximately 60 seconds from the dispensing step. Alternatively, the recording step may be begun within approximately five minutes from the dispensing step. The method further included the step of measuring the current and applying a leak subtraction data acquisition protocol.

The parallel patch clamp system of the present invention has other features and advantages which will be apparent from or are set forth in more detail in the accompanying drawings, which are incorporated in and form a part of this specification, and the following Detailed Description of the Invention, which together serve to explain the principles of the present invention.

BRIEF DESCRIPTION OF THE DRAWINGS

FIG. 13A and FIG. 13B are graphs illustrating currents measured using a single aperture technique and the PPC technique of the present invention, respectively.

FIG. 15 is a graph illustrating success rates for individual wells in single-cell and PPC modes.

FIG. 17 is a graph illustrating a prediction of open apertures and all other apertures.

DETAILED DESCRIPTION OF THE INVENTION

Figure 1:
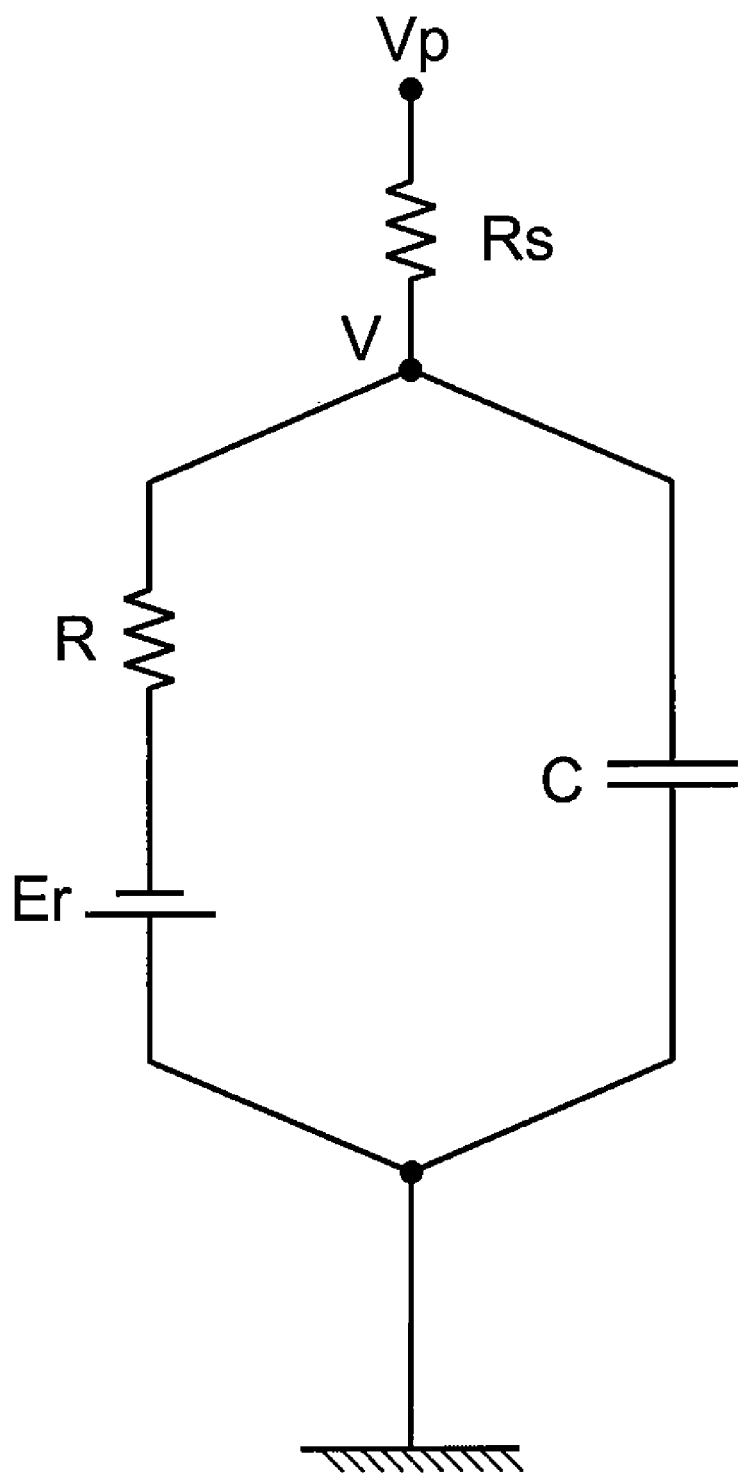
FIG. 1 is a schematic drawing showing an equivalent circuit for a simple cell.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

The present invention provides systems, including apparatus and methods, for performing parallel patch clamps. These systems may (i) increase the success rate per well, (ii) improve the throughput, (iii) improve the data consistency, (iv) lower the cost per data point and (v) in the case of add-and-read systems, expand the potential electrophysiological applications to include LGICs. The systems include the concept of measuring whole-cell currents in a large number of cells patch clamped to many holes within a single well. The device, in turn, may have one or more wells, and may be used for single experiments and/or multiple experiments, for example, efficient high-throughput screening. The systems may be capable of working regardless of whether or not all the holes within a single well are electrically sealed. For the purpose of the present invention, the term "sealed" will be understood to mean electrically sealed as understood in the field of electrophysiology in its broadest context. One will appreciate that the term "sealed" encompasses the physical state in which a membranous sample is sufficiently bound to an aperture to allow for the extraction of meaningful data.

The present invention also provides improved systems, including apparatus and methods, for estimating electrophysiological parameters, particularly when compensation of one or more of these parameters has been enabled.

For clarity, the following definitions are used throughout.

a. Ion channel—A membrane-associated biological mechanism, passive and/or active, such as a membrane protein, for facilitating the passage of ions across biological membranes, including but not limited to conventional ion channels, such as voltage or ligand gated ion channels, as well as ion transporters and other ion flux mechanisms found in biological and/or synthetic membranes. The ion channels may facilitate passage of ions into and/or out of cells, organelles, and so on, and/or across synthetic membranes, such as vesicles, suspended lipid bilayers, and so on.

b. Patch clamp—a mechanism for recording ion-channel properties from patches of membrane, including biological and/or artificial membranes. These properties may include voltage and/or current properties, among others, including current changes in response to voltage clamping and/or voltage changes in response to current clamping. The term is used here as an example only. The systems described herein more generally may be used with any suitable electrophysiological recording techniques. The patch clamp technique may include pipette-based patch clamp techniques, for example, as described in the above-mentioned *The Axon Guide, Single Channel Recording*, and *Ion Channels of Excitable Membranes*, all of which are incorporated herein by this reference, and automated patch clamp techniques, for example, as described in the U.S. patent application Ser. No. 10/236,684 filed Sep. 5, 2002 (now U.S. Patent Application Publication No. 2003/0070923 A1), and U.S. patent application Ser. No. 10/334,815, filed Dec. 31, 2002 (now U.S. Patent Application Publication No. 2003/0146091 A1), the entire content of which applications is incorporated herein by this reference.

c. Data Point—A measurement from one compound at one concentration, whether it is a single response from one cell or an averaged response from two or more cells.

d. Throughput—The number of data points per time period, most usually an 8-hour day.

e. Well or Chamber—A single compartment in a multi-compartment structure. Well and chamber are used interchangeably. For example, a single well in a multi-well plate is also referred to as a chamber.

f. Cell or Cell Membrane—A biological entity that includes ion channels, transporters, and ion flux mechanisms. A cell can be an intact biological cell or organelle, or a cell membrane fragment or synthetic membrane that includes an ion channel, transporter, or ion flux mechanism.

g. Partition—A structure that separates two opposing wells or chambers thus forming, in part, a multi-compartment structure, and that may include one or more apertures for binding cells or cell membranes for analysis. The terms substrate and partition may be used interchangeably. The structure may be distinguished from a pipette tip in having an extent transverse to any associated apertures that is at least as significant and that typically is at least several times as significant as the diameter (or characteristic width) of the aperture. The structure may be at least substantially planar, particularly in the vicinity of any associated apertures (such as the region surrounding the aperture involved in binding cells and/or cell membranes).

h. Pipette Patch Clamp—Conventional patch clamp system, in which a pipette forms a seal with a membrane, for example, as exemplified by Sakmann and Neher (see the above-mentioned Single Channel Recording).

i. Planar Patch Clamp—New patch clamp system, in which a typically planar substrate (e.g., as defined above) forms a seal with a membrane, for example, as exemplified by the above-mentioned U.S. patent application Ser. No. 10/334,815, filed Dec. 31, 2002 (now U.S. Patent Application Publication No. 2003/0146091 A1), the entire contents of which is incorporated herein by reference.

j. Units—Gohm=$10^9$ ohms, Mohm=$10^6$ ohms.

k. Ensemble current—For the purposes of the present invention, and in addition to conventional definitions, the term "ensemble current" may refer to the total measurement of the currents in cells sealed to an array of measurement apertures (up to one cell per aperture) in each well of a microplate using a single voltage clamp amplifier per well (e.g., "ensemble current of a well" in addition to the conventional "ensemble current of a cell"). In addition, the term "ensemble current" may also refer to the total measurement of currents through an array of measurement apertures whether or not all apertures are sealed with a cell (e.g., one or more open or partially occluded apertures).

l. Membranous Sample—A biological entity that includes an ion channel, transporter, or ion flux mechanism. The entity may be a cell, a vesicle, an organelle, a cell membrane fragment or a synthetic membrane.

Figure 2:
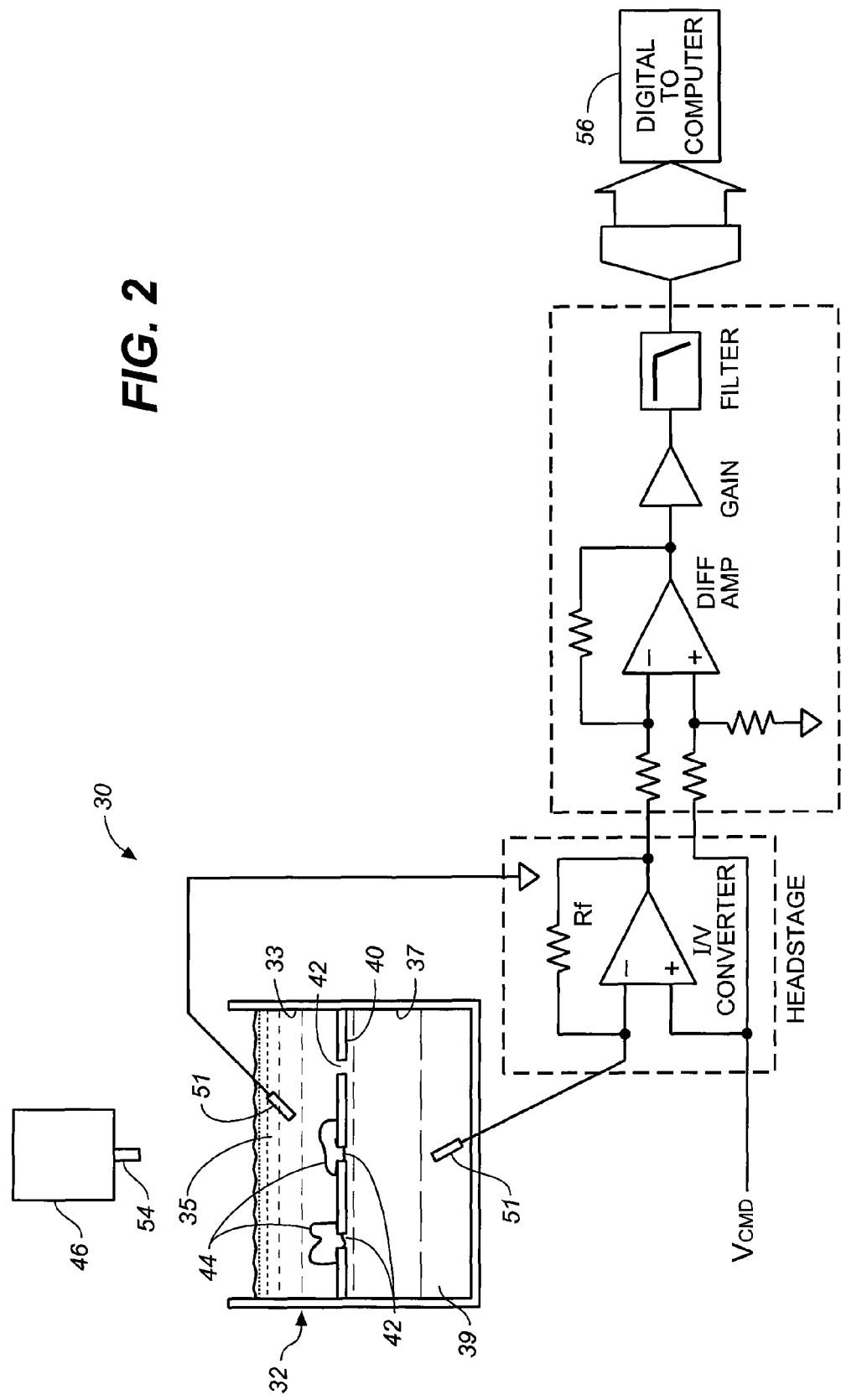
FIG. 2 is a schematic cross-sectional view of an exemplary parallel patch clamp (PPC) device in accordance with the present invention.

Turning now to the drawings, wherein like components are designated by like reference numerals throughout the various figures, attention is directed to FIG. 2 which shows a parallel patch clamp (PPC) system in accordance with the present invention, which is generally designated 30. For the purposes of the present invention, parallel patch clamping refers to patch clamping in which current flows in parallel between two or more apertures from one chamber to the other. The currents passing through each aperture are generally not equal but they are parallel to one another.

The PPC system includes one or more wells 32 (a single well is show in the figure). A top (extracellular) chamber 33 is filled with a conventional extracellular solution 35. A bottom (intracellular) chamber 37 is filled with a conventional intracellular solution 39, though this solution may have additional reagents added as discussed further below. The terms top and bottom are used here for convenience; there is no requirement that the chambers be physically oriented in such a manner. The extracellular and intracellular chambers thus form a multi-compartment structure.

Separating the two chambers is a partition 40 with at least two or more holes or apertures 42 that pass through the partition and allows electrical connectivity between the two chambers. The holes may be about 0.2 µm to about 20 µm, and preferably about 0.5 µm to about 5 µm in diameter, although they more generally may be of other suitable sizes. The partition is typically about 10 µm to about several millimeters thick, although it more generally may be of any suitable thickness. Attached to each well are conventional electrophysiology electronics that are used to stimulate and record from cells that have been placed in the top chamber. The cells 44 are added to the extracellular chamber and are directed to the holes in the partition and form an electrical seal with the partition in the vicinity of the hole.

The PPC device has multiple holes per well, and can work even if not all the holes are sealed by a cell. More specifically, the PPC device will work if current is able to flow from the top to bottom chamber not only through (a) ion channels or transporters residing in cells that are sealed to the partition, but also through (b) open and/or partially occluded holes.

There is generally no restriction on the number of wells that can be present in a single consumable of a PPC device, although the most common configurations are those that are complementary with existing high throughput screening devices, for example, 96, 384, 1536 wells per consumable, among others.

Several features of the PPC device are discussed below in detail.

Fluidics

The PPC device optionally may utilize a suitable fluidics system 46, for adding samples, reagents, and/or the like to wells.

The fluidics system may include add-and-read fluidics, in which fluid and/or other materials are added, and then a result is detected or read. In some cases, it may be important to measure the voltage-clamp current and/or other parameters continuously or sampled before, during and/or after the control and test compounds are added, since LGIC responses usually desensitize.

The fluidics system also may include add, read, and wash fluidics, for example, using a random access fluidics approach. This approach maximizes the flexibility of the PPC device, but may reduce the throughput of the device.

Figure 7:
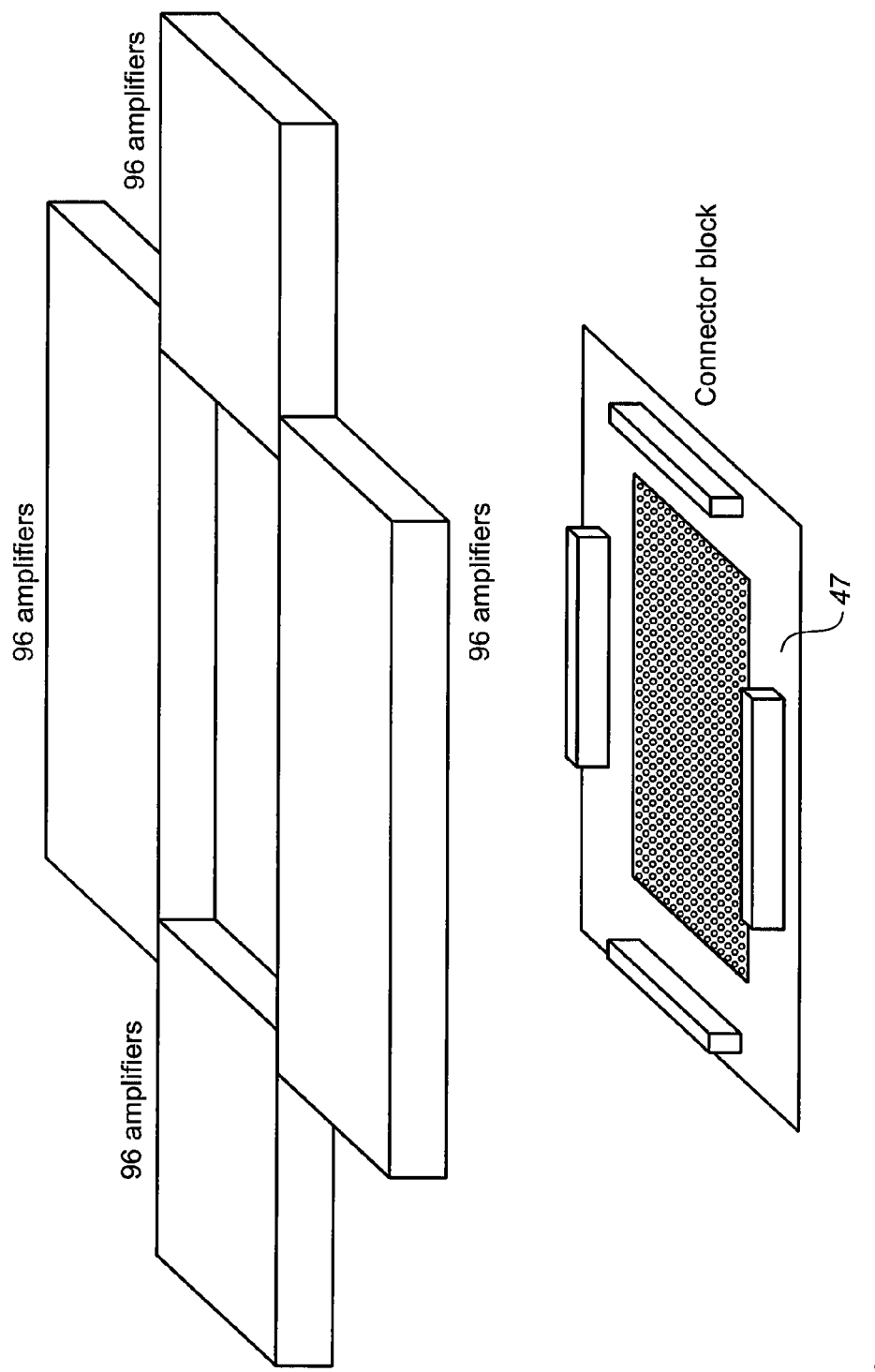
FIG. 7 is a schematic top view of an exemplary replaceable electrode plate with holes for compound addition (check pattern) and surrounding amplifiers in accordance with the present invention.
Figure 8:
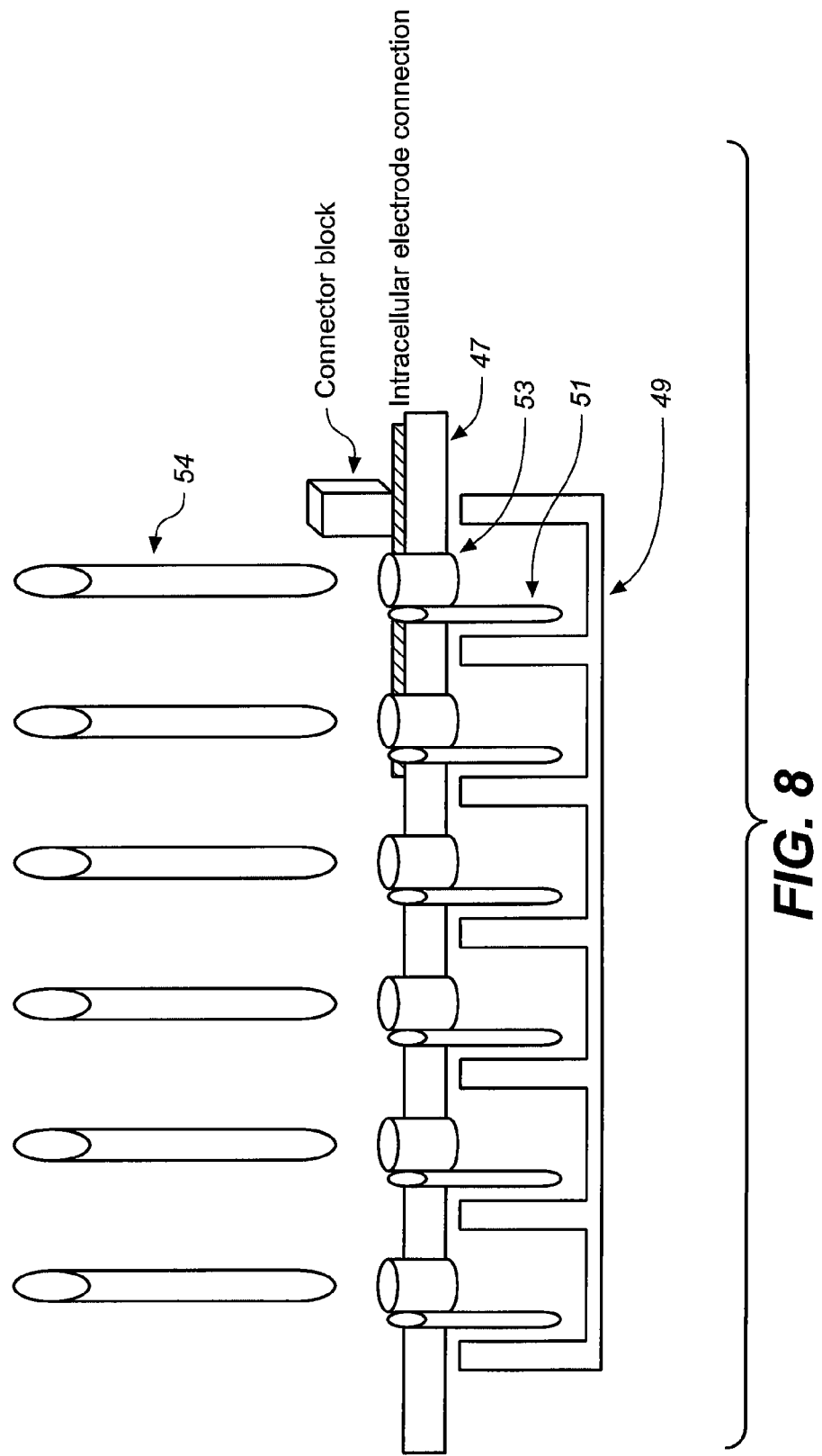
FIG. 8 is a schematic side view of an exemplary electrode plate showing an example of a connecting wire. Extracellular electrodes project into each chamber in accordance with the present invention. An access hole allows the fluid dispense tubes to inject compounds into the chambers.
Figure 9:
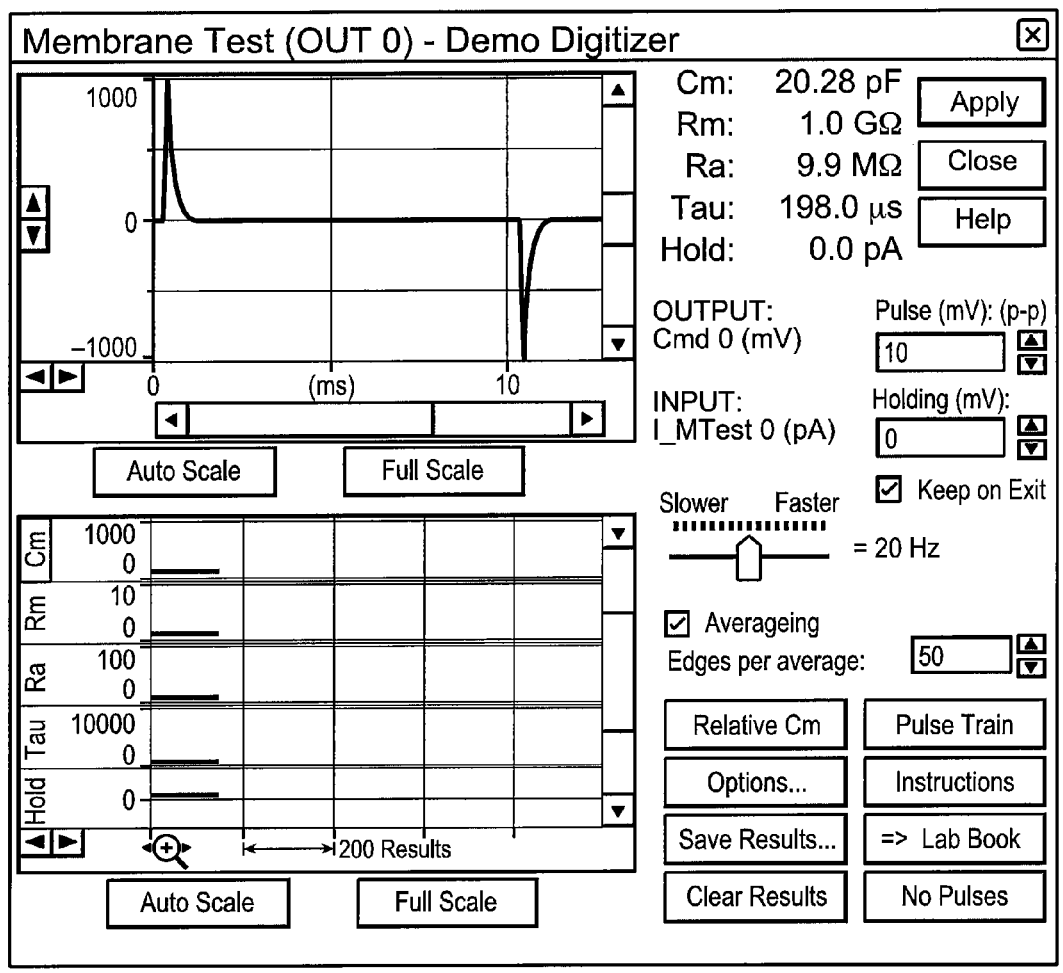
FIG. 9 is a screen capture of Membrane Test from pClamp software, Version 9.1.

In some embodiments, solutions are dispensed while continuously voltage clamping and recording currents. FIG. 7 and FIG. 8 show one embodiment of the chambers of a PPC system. A removable electrode plate 47 could be used above a PatchPlate™ or other suitable multi-compartment structure such as a microplate 49 that includes a plurality of wells 32. Preferably, this configuration would have individual conducting wires to join each electrode 51 to its corresponding amplifier. Preferably the electrodes are Ag/AgCl, however one will appreciate that the electrodes may be graphite, platinum or other suitable materials. Each electrode would dip into an extracellular chamber 33 in the microplate. A hole 53 above each microplate chamber would allow the dispenser tubes 54 of the fluidics system to add test compound to the chamber. The electrode plate could be washed before each new microplate is added to the instrument or a set of electrode plates could be used one per microplate during the course of the day and washed or replaced. If necessary, any replenishable electrodes such as Ag/AgCl electrodes could be replenished on a daily or less frequent regular basis.

Chambers and Partition

For a given well, there is typically an intracellular chamber 37 that opposes an extracellular chamber 33, and the chambers are separated by partition 40 (FIG. 2). There may be a single extracellular chamber for each intracellular chamber, or there may be a common chamber for a group of opposing chambers. For example, there may be several independent extracellular chambers and a single intracellular chamber, or a sub-set of extracellular chambers that are serviced by a single intracellular chamber.

The partition that separates an intracellular chamber from an extracellular chamber contains at least one hole or aperture 42 that passes through the entire partition. In the PPC device of the present invention, there are several apertures per extracellular well, preferably greater than 1 hole per well, more preferably greater than about 10 holes per well, yet more preferably 64 holes per well, and most preferably greater than about 100 holes per well, and may be greater than 1000 holes.

The holes in the partition may be fabricated in a process whose cost is not proportional or minimally proportional to the number of holes. Alternatively, or in addition, the cost per hole may be small relative to the cost of the entire consumable plate that comprises many wells. For example, if the partition is made from etched silicon, the price per unit area will be independent of the number of holes.

The partition may be made from any suitable material(s), including but not limited to plastic, glass, silicon, and/or a polymer such as Sylgaard. The holes may be fabricated in the partition using techniques known in the art. Typically, the diameters of the holes may be about 0.2 μm to about 20 μm, and preferably are about 0.5 μm to about 5 μm. The thickness of the partition is typically about several microns to several millimeters thick. However, as discussed above, the diameters of the holes and the thickness of the partition may more generally include any suitable values. Photolithography approaches may be used to etch holes in silicon. Alternatively, laser drilling approaches may be used to fabricate holes in glass or plastic. Such laser drilling processes are well known in the art. However, typically, laser drilling involves the sequential formation of individual holes. Additionally, laser drilling in glass or plastic for conventional automated patch clamp devices may require careful control of laser parameters to ensure properly sized and shaped holes (e.g., diameter, taper of the hole, surface texture, etc.) Therefore, increasing the number of holes in the partition linearly increases the cost of the partition. One will also appreciate that the holes may be formed by other suitable means including, but not limited to, molding, embossing and/or chemical etching.

The PPC approach does not require high resistance seals (i.e., Gohm) between a cell and the surface around a hole. In this situation, the quality (e.g., diameter, taper of the hole, surface texture, etc.) of the hole is not as critical. Therefore, in some cases it may be possible to (i) reduce the complexity of the laser drilling process, and/or (ii) laser drill holes in parallel, both of which greatly reduce the cost of the partition. For example, it may be possible to split the laser drilling beam into several sub-beams, where each sub-beam is capable of forming a hole in the partition. In a preferred embodiment, all the holes within the partition could be formed in a single laser beam exposure, thus eliminating the dead time needed to move a laser beam from putative hole to putative hole. Alternatively, a single exposure from the laser beam may be used to fabricate a subset of holes within the partition, for example, all the holes within a single well. The laser beam would then be scanned over the entire partition until all the holes associated with each well have been fabricated. While not as efficient as a single exposure, the latter approach is more efficient than a completely sequential process.

The surface of the partition around the hole, and possibly including the surface of the walls of the hole in the partition, may be modified to facilitate seal formation between the cells and the partition. There are a number of approaches to modify such surfaces to enhance seal formation, including smoothing the surface of the hole with heat, cleaning the surface, modification of the charge on the surface, immobilization of cell adherent molecules such as polylysine to the surface, and so on. Exemplary approaches are described in the above-mentioned U.S. patent application Ser. No. 10/334,815, filed Dec. 31, 2002 (now U.S. Patent Application Publication No. 2003/0146091 A1), the entire contents of which is incorporated herein by reference.

Electronics

Electrodes are used in electrophysiology to measure voltage and to pass current. A common source of error in any electrophysiological recording configuration is voltage drift in the junction potential of the intracellular and extracellular electrodes. One will appreciate that the term "potential" may be used synonymously with the term "voltage" and encompasses any electrical voltage difference between two points. Voltage drift of more than a few millivolts can lead to erroneous determination of the activation thresholds of the cellular currents under study, or shifts in the holding potential that can ultimately lead to premature deterioration of the cell viability.

Solid electrodes are typically used in electrophysiology, and Ag/AgCl electrodes are commonly used because they drift less than most other solid electrodes. Nevertheless, Ag/AgCl electrodes that are initially stable often start to exhibit unacceptable drift after a period of use. One of the contributors to the development of voltage drift is the total current per unit surface area (i.e., current density) passed by the electrode, especially if the current is predominantly of one polarity. Large instantaneous current densities might also contribute to the development of voltage drift of either a transient or permanent nature.

Drift problems may be reduced or minimized using any suitable techniques. Such techniques include but are not limited to large-area electrodes and/or two-terminal virtual grounds.
  a. Large area electrodes—These can reduce or minimize the current density.
  b. Two-terminal virtual ground—This is a technique that is not commonly used. It is usually only implemented for a specific electrophysiology configuration known as a two electrode voltage clamp of large cells such as oocytes. In this approach, the current passing and voltage recording functions are separated and assigned to two different electrodes. The voltage recording electrode is typically made from Ag/AgCl and the current passing electrode is typically made from a pure metal. Junction potentials in the current passing electrode are irrelevant, even if they vary substantially.

The problems of voltage drift described above are present to some extent in all electrophysiological recording situations but are likely to be worse when large currents are passed through the same electrode that is used for voltage recording. In prior automated patch clamps, a single electrode is used for intracellular voltage recording and current passing, and another single electrode is used for extracellular voltage recording and current passing. The current-induced voltage drifts are not a major problem because the currents through a single mammalian cell such as is typically used in a automated patch clamp are small, of the order of a nanoampere. However, the coatings on electrodes do wear out with time and to the extent that this wear is caused by current flow, standard patch clamps would benefit from a technique that eliminated the current from the voltage recording electrode.

In the present case of a parallel patch clamp system, the currents in each chamber could be one or more microamperes leading to very high current densities, and in some cases, thousandfold higher current levels. At this many times current level the drift problems are likely to be either immediately worse, or commence much sooner.

In some embodiments, the drift problem can be ameliorated in the extracellular side (top side) by using a large area electrode in contact with the extracellular solution. It can be further ameliorated by using one-time or few-time use disposable electrodes or electrodes that can be replenished. Alternatively, or in addition, this problem can be ameliorated on the intracellular side similarly. In the special case that the intracellular side is a large plenum (like that used in the IonWorks® HT system) instead of using a single electrode several or many tens of electrodes could be used in parallel to reduce the current density per electrode.

Figure 4:
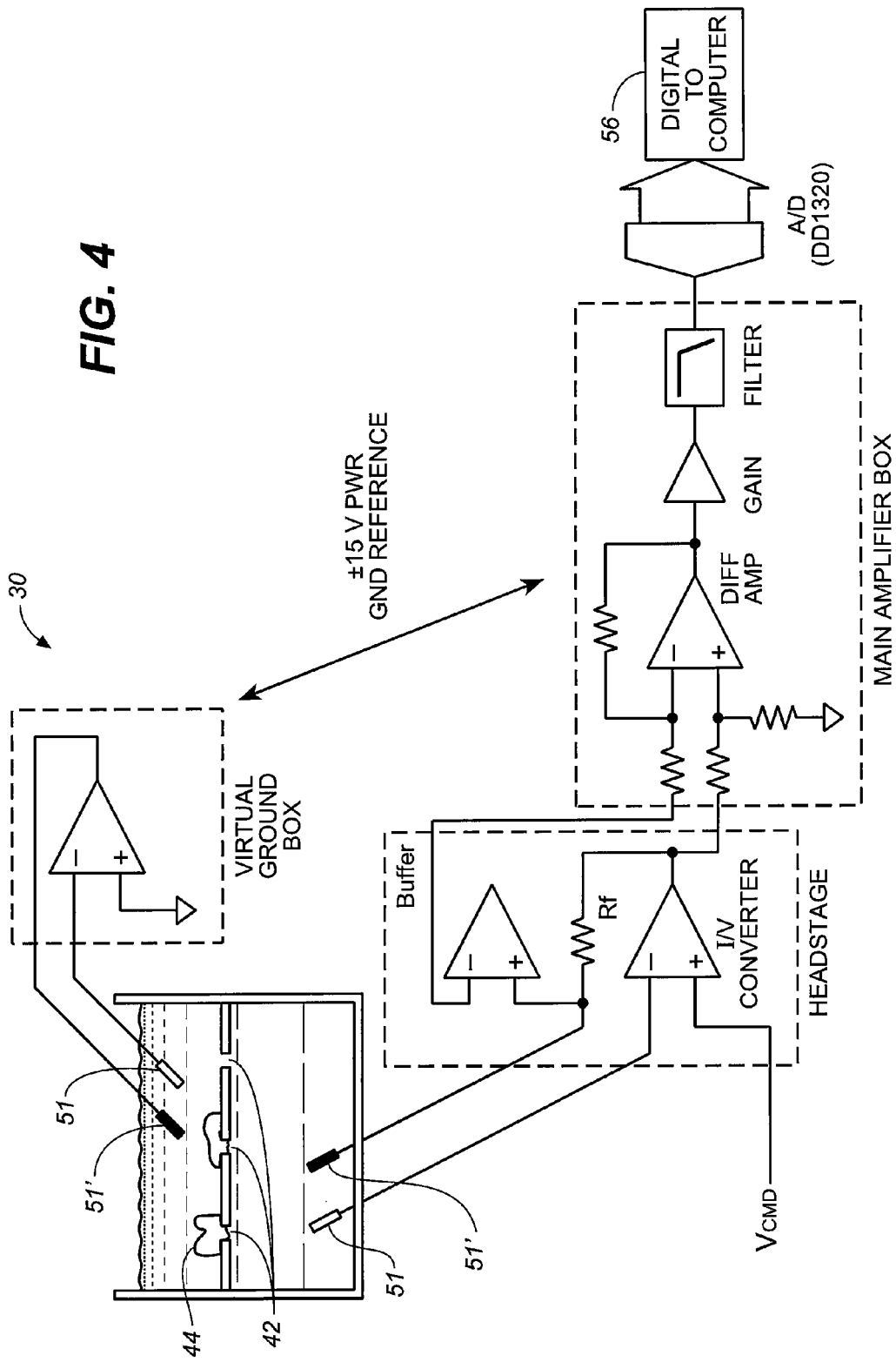
FIG. 4 is a schematic cross-sectional view of another exemplary PPC device in accordance with the present invention including virtual ground dual electrodes.

In some embodiments, the current passing and voltage recording functions are separated for both sides of a partition (see, e.g., FIG. 4). In each case, the existing electrodes are replaced by a pair of electrodes, where one is a electrode 51 used solely for voltage recording and the other is a electrode used for current passing 51'. Alternatively, a pair of electrodes may be used on only one side of the planar substrate, and a conventional single electrode may be used on the alternate side. While the preferred electrode configuration is described in the context of a parallel patch clamp configuration, one will appreciate that such configuration may also be used in a conventional pipette based patch clamp.

Figure 5:
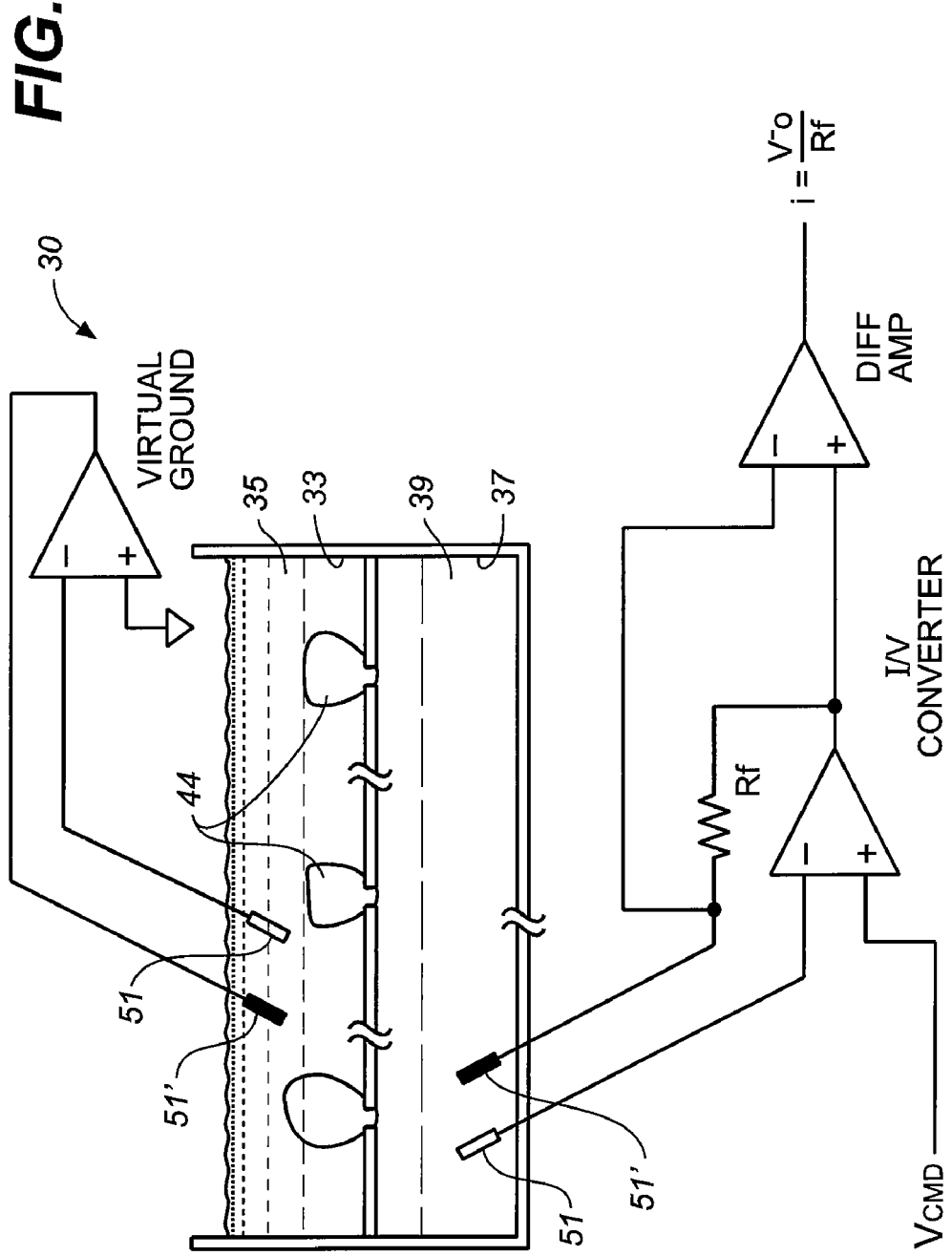
FIG. 5 is a schematic cross-sectional view of another exemplary PPC device in accordance with the present invention having two-electrode amplifiers in extracellular and intracellular compartments.

One will appreciate that separating the current passing and voltage recording functions in the electrodes on both sides of the substrate may also be used in cases where cells occlude all apertures (see, e.g., FIG. 5).

A practical limitation of the dual two electrode configuration is that two electrodes have to be physically placed where previously only one was required. However, since the voltage recording electrode does not pass any current, it does not have to be sized with consideration of keeping the current density low, so it can be as narrow as is compatible with structural considerations. Similarly, since the current passing electrode does not record voltage it does not matter how high the current density is (provided that it is not so high as to cause bubbles to form) and in general this means that the current passing electrode can also be narrow.

In some embodiments, the current passing electrode can be made of almost any metal, such as but not limited to platinum, gold, tungsten, silver and stainless steel. Assuming that the electrodes will be in contact with non-flowing solutions for extended periods of time, the metal should be chosen to have minimal toxic effects. It is possible for electrolysis to occur at the metal surface. Experience with oocyte voltage clamps has shown that platinum suffers less from this problem than does gold.

Methods of Use

Cells are dispersed into the wells, for example, from a robotically controlled dispense head of the fluidics system 46, and fall and/or are directed under gravity and/or other passive and/or applied forces to the substrate 40. Preferably, cells are dispensed from a solution of cells in suspension. Preferably, about 1,000 to 10,000 cells, and preferably at least 5000 cells and in some cases as much as 200,000 cells, are dispensed into each well where each well contains about 1-100 µl of solution. Preferably the ratio of the cells to apertures is greater than 1:1 and may be 1:10, 1:100, 1:1000, 1:10,000 or 1:100,000. These cells then settle on the substrate under gravitational force, although other forces may be utilized. Cells may also be grown directly on the substrate. An important aspect of the PPC device is that there is not a requirement that all holes are occluded within each well. Therefore, if a solution of cells is dispensed within a well, not all holes have to be covered by a cell. Alternatively, if cells are grown within the wells, for example, using conventional cell culture techniques, it is not a requirement that cells reach confluence and occlude each hole. Cells that were in solution that are dispensed into each well, are recorded from shortly after dispense, typically within about a few seconds to several minutes. For example, recording may begin within about one, two, three, four or five minutes from dispensing, and even within approximately 60 seconds from dispensing.

In addition to gravity that allows cells to settle passively on the substrate, the cells may be directed to the holes through alternate attractants. Such attractants include but are not limited to electric fields, chemoattractants, and suction or positive pressure. Preferably gravity is used to allow cells to migrate to on or near the surface of the substrate. A small amount of suction will be used to attract the cells to the holes. Exemplary mechanisms for applying suction and electric fields are disclosed in U.S. Pat. No. 6,776,896 and the above-mentioned '815 application, the entire content of which patent and application are incorporated herein by reference.

An important aspect of the present invention is that the present PPC approach works with or without a requirement for high-resistance seals. For example, the PatchXpress® 7000 system typically achieves seal resistances in excess of about 1 Gohm. The IonWorks® HT system achieves seal resistances in the range of about several hundred Mohms. The PPC instrument can tolerate very low resistances, on the order of about 10's of Mohms, and can even tolerate multiple open holes in the substrate, where each hole may have a resistance of about several Mohm. Therefore, there is no longer a requirement for high resistance seals, a feature that has been noted as essential in the prior art (see, e.g., the above-mentioned U.S. Patent Application Publication No. US 2002/0053915 A1).

Electrical stimulation and recording of signals from each well may be placed under software control by a computer 56. The general approach to stimulating and recording ion channel activity in single-aperture patch clamping is known in the art. In a multi-well PPC device, the preferred embodiment is a method of stimulating and recording from wells in a synchronous fashion, more specifically, each well is exposed to the same electrical stimulation and recording protocol at the same time. This approach simplifies the design of the instrument and eliminates any capacitive cross-talk that may occur due to the density of the electrodes within the multi-well plate. Alternatively, each well could be stimulated and recorded from independently. In the event that useful data cannot be collected from all wells (e.g., in the event of a mechanical error, or a solution dispensing error that renders a well useless), the asynchronous approach ensures that reagents are only applied to wells that are capable of returning useful data. The asynchronous approach is potentially a more cost-effective method to screening a library of compounds, wherein costly reagents are only utilized in wells that return useful data. However, the asynchronous approach is more complicated, and may suffer from capacitive cross talk.

The PPC approach may be used in methods of screening LGICs in which separate wells are used to measure control responses from test responses. In an add-and-read system, it is typically not possible to assay LGICs because it is necessary to add an agonist to determine the control response, then wash it out before adding the test compound (typically a mixture of test compound and agonist). In a non-preferred embodiment, the control response is measured from a single cell in a first well and is compared to a test response from a different cell in a different well. However, the variability in the expression level of ion channels in a given cell and the inherent biological variability associated with each cell (for example, cell health, cell size, etc.) typically precludes this approach from being preferred.

The preferred embodiment of the present teachings is to assay LGIC's by determining a control response from one or more control wells, where each well contains multiple cells and multiple holes. The agonist is applied to each control well and the control response is measured. For example, there may be positive and negative control compounds that should elicit known responses. The test responses to test solutions (typically agonist and test compound) are measured from different test wells, where each test well contains multiple cells and multiple holes. The effect of the test compound is evaluated by comparing the response measured from the test wells to the response measured from the control wells. If the number of holes per well in the control and test wells that are being recorded from is sufficiently high, the variability of the system is reduced to an acceptable level.

With respect to the term "sufficiently high", this term is likely to be assay or experiment dependent. If the inherent variability of the cells is high, then the number of holes per well must also be high to ensure statistically significant values are obtained from the cells being recorded from. For example, if the level of functional ion channel expression in a particular cell line varies widely, it could be necessary to have a large number of holes per well to ensure that any measured change in response is due to an experimental manipulation, and not due to inherent variability in functional ion channel expression. It follows that for cell lines that express functional ion channels at a relatively uniform level, the number of holes per well can be reduced. Functional ion channel expression is used above solely as one example to demonstrate that the term "sufficiently high" is likely to be assay or experiment dependent. There are other factors that need to be considered when determining suitable or optimum numbers of holes per well.

The PPC approach also may be used in methods to assess functional ion channel expression in a population of cells. For example, using conventional patch clamp procedures, it is costly and time consuming to assess the efficacy of ion channel mutation experiments. Generally, a genetic manipulation such as an amino acid insertion, deletion, or change, is performed that results in a modification to ion channel function. Assessing the impact on ion channel function may require laboriously patch clamping multiple cells until a statistically valid analysis can be completed. More specifically, if the genetic manipulation is a manipulation that alters the voltage sensitivity of a voltage activated ion channel, a single cell is patch clamped, and appropriate voltage clamp acquisition and analysis protocols are executed. This process is repeated on multiple cells until statistical significance is reached. This is a costly and time-consuming process using conventional patch clamp techniques. Using the PPC approach, a large number of cells from a population of cells that have been genetically manipulated can be assayed in a single well exposed to a single set of voltage protocols. The result is a statistically valid analysis that can be completed based on a single experiment.

The PPC approach also may be used with only a single well instead of multiple wells. Typically, the PPC approach is used in a high throughput fashion to maximize the speed of assaying ion channel function. An important feature of the PPC approach is the realization that the "yield" of the PPC method can approach 100%. For example, in a typical patch clamp experiment on a single cell, the success rate may be about 50%. In a PPC procedure, the success rate, or yield, may be about 100%, since it is more likely that at least one hole will be covered, and since data can be collected even if some holes are uncovered. This increase in yield translates into an increase in efficiency. In addition to time savings, this increase in yield may allow for the execution of experiments that may not have been possible with labile, limited-supply reagents, such as isolated proteins or peptides.

Using the PPC with Open or Partially Occupied Holes.

When using gravity and suction to direct cells to holes, there may be a percentage of holes that will not be tightly sealed with a cell. One aspect of the present teachings is the realization that while it is desirable to block every hole, it is not necessary for every hole to be blocked for the PPC approach to work. In the event that a percentage of the holes remain open, a number or problems may occur. The effect of each of these problems, however, can be reduced or eliminated utilizing the PPC approach of the present invention.

Since a conventional voltage clamp circuit will be used to measure the ensemble current through all the holes in the substrate, whether they are open, occluded in any fashion, sealed by a bead, or sealed by a cell, there may be corruption of the ensemble whole cell current. Specifically:

a. There may be a large electrical leak current through the unblocked holes that might be larger than the combined current through the sealed and patch clamped cells within the same well. This electrical leak may be a linear effect.

b. There may be a smaller electrical leak current through the occupied holes that do not have sealed or whole cell configuration cells. This electrical leak also may be a linear effect.

These two electrical leaks may (i) reduce the signal-to-noise ratio and (ii) substantially obscure the ion channel currents. Typically, the noise cannot be reduced, but in general the signal through the ion channels of the whole cell clamped cells will exceed the noise, making a sufficiently accurate measurement possible.

In the case of electrical leak, this can be removed by a leak subtraction data acquisition protocol, among others, in which the ohmic leak is first measured for small, non-activating control voltage steps and then subtracted from the responses to the test commands, using a technique called passive subtraction. See, e.g., *leak current subtraction method for Ion-Works™ HT—IONWORKS HT TECHNICAL NOTE # 1*, by Molecular Devices Corporation.

In an alternate embodiment, p/n leak subtraction could be used. In this approach, small, non-activating control voltage steps are applied to the cell and then the waveform of the response to these control voltage steps are scaled and subtracted from the responses to the test commands. In contrast to the passive subtraction technique above, which only removes the ohmic leak, this p/n subtraction protocol also reduces the capacitance contributions. This type of p/n subtraction is implemented in pCLAMP software from Molecular Devices Corporation, the industry standard electrophysiology data acquisition and analysis software package.

Additionally, the amplifier dynamic range (i.e., the range of acceptable currents that can be recorded by the patch clamp amplifier) can be set to anticipate a contribution from the electrical leak. This is typically done by altering the magnitude of the feedback resistor. For example, if the headstage feedback resistor is too large for the measured current, the headstage will saturate. For the large leakage currents possible in the PPC device, it is preferable to reduce the feedback resistor to about 50 Mohm from about 500 Mohm, or more preferably to reduce the feedback resistor to about 5 Mohm. The preference is to reduce the feedback resistor in proportion to the number of apertures, for example, to about 500/n, where n is the number of apertures. Most preferably, the feedback resistor will be reduced to a value that allows for recording from each well without saturation of the headstage while using a substantial fraction of the amplifier's dynamic range with typical signals. It is well known in the art to decrease the feedback resistor of a conventional patch clamp amplifier when switching from recording small (picoamperes) currents from single channels versus recording larger (hundreds of picoamperes or nanoamperes) whole-cell currents. Conventional patch clamp amplifiers, such as the MultiClamp 700B amplifier from Axon Instruments/Molecular Devices Corporation, offer the ability to select the feedback resistor from one of four values: 50 Gohm, 5 Gohm, 500 Mohm, or 50 Mohm.

In addition to the electrical leak problems outlined above, there may be a substantial fluidics leak as extracellular solution is sucked through the holes into the intracellular chamber.

In the case of such fluidics leak, the amount of leakage may be reduced by reducing the amount of suction, for example, by using the smallest amount of suction necessary. Its impact could also be reduced or eliminated by using a larger intracellular space, or by exchanging the intracellular solution continuously or at a critical time after seal formation. In the event that positive pressure is applied from the intracellular chamber, which would result in intracellular fluid contaminating the extracellular fluid, the extracellular fluid could be exchanged, or the initial volume of the extracellular fluid could be increased to minimize such a contamination effect.

Using the PPC with Cells in a Variety of Conditions.

The cells that occupy holes in the whole-cell configuration PPC device may be in a variety of physiological states and/or under a variety of conditions.

a. Healthy cells with good ion channel expression levels and a good time course of heterologous current. These cells would exhibit small electrical leak that is stable over medium time courses.
b. Healthy cells with poor or no ion channel expression. These cells would exhibit small electrical leak that is stable over medium time courses.
c. Cells that are electrically leaky and have a variety of expression levels. These cells would exhibit larger electrical leak that might not be stable over medium time courses.

The stable electrical leak can be dealt with by passive leak subtraction, for example, as outlined within. In a preferred embodiment, the unstable leak current can be dealt with by passive leak subtraction, especially if (i) the correction factor is calculated immediately prior to each measurement sweep, and (ii) the measurement sweeps are short compared to the time course of the instability.

Using the PPC with Approaches to Reduce the Number of Open Holes.

Figure 3:
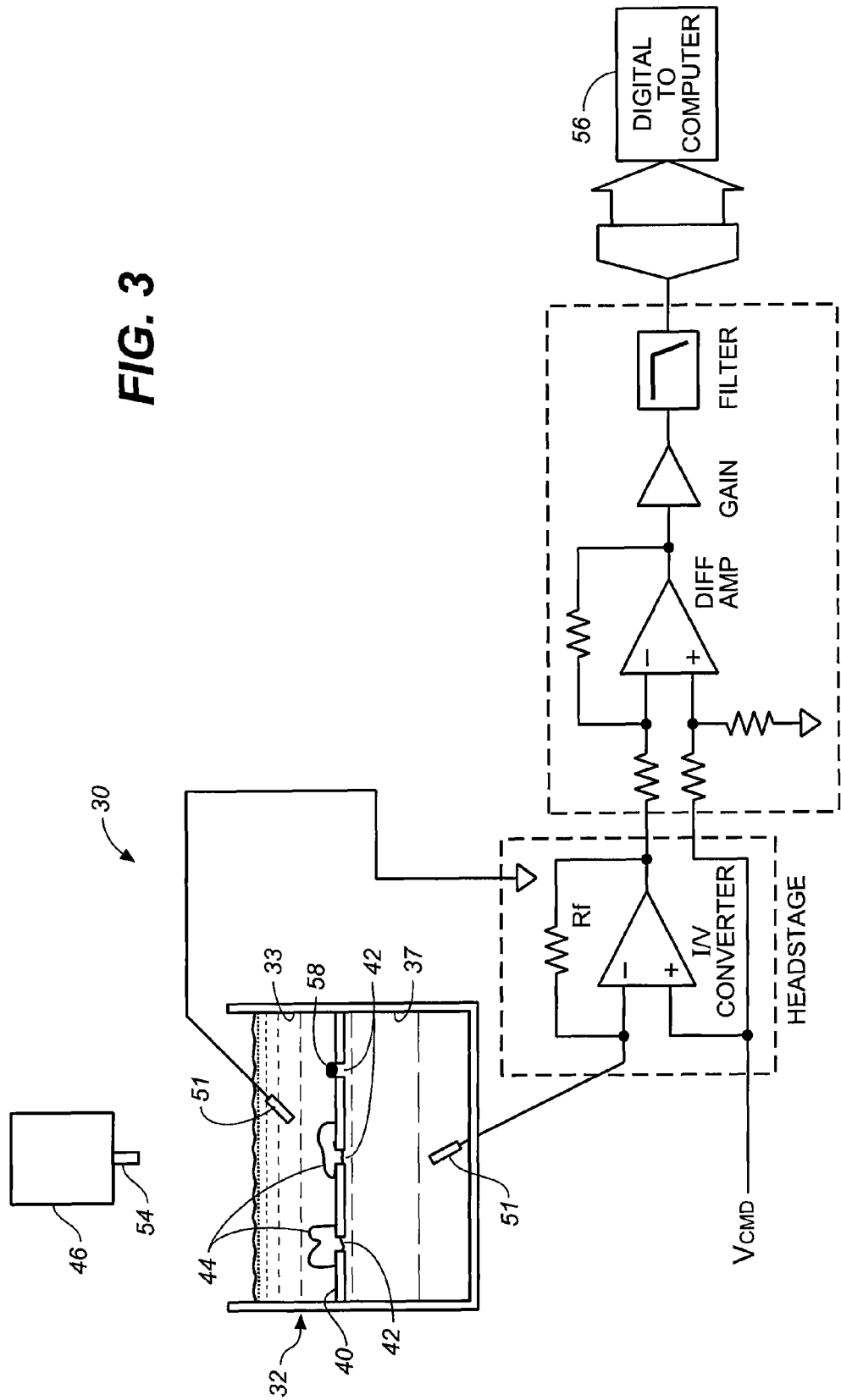
FIG. 3 is a schematic cross-sectional view of another exemplary PPC device in accordance with the present invention illustrating blockage of open holes with blocker beads.

In one embodiment of the present teachings, a quantity of small beads 58 is introduced into each well shortly after the cells are introduced (see, e.g., FIG. 3). These beads are slightly greater in diameter than the diameter of the holes, and they are denser than the aqueous solution. The beads could be made of glass, poly dimethyl siloxane (PDMS), plastic, polystyrene, Teflon®, and/or any other non-conductive material that does not (substantially) sequester drugs. The beads could be made of metal and coated with one of the previous materials. The beads could be made of a material that has a non-conductive surface but that is permanently electrically polarized.

The beads drift and/or otherwise find their way or are directed to the bottom and may be attracted to the unoccupied holes by the same suction that attracted the cells. The beads serve to block open holes. (FIG. 3).

Figure 6:
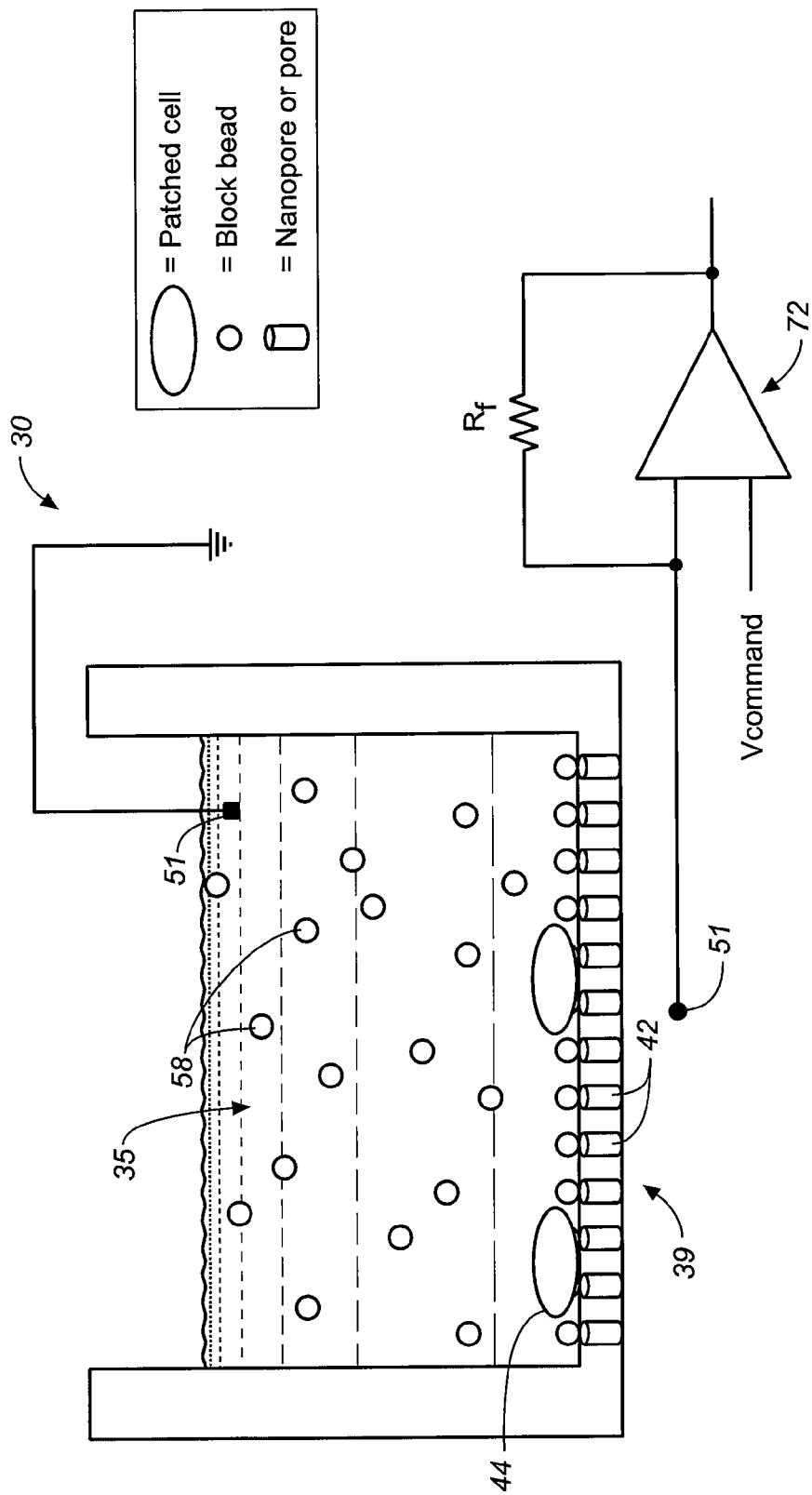
FIG. 6 is a schematic cross-sectional view of another exemplary PPC device in accordance with the present invention including a partition having nanopore-sized holes and multiple holes per cell, and illustrating the optional use of blocker beads.

Ordinarily, the diameter of the pores used in automated patch clamping is between about 0.2 µm to 20 µm. In a further alternate embodiment, standard nanopore membranes with a large number of sub-micron holes are utilized (see, e.g., FIG. 6). These holes might be too small to enable whole cell access using suction, but could work if whole cell access is achieved by exposing the membrane to an antibiotic such as amphotericin. In this approach, there may be more than one hole per cell. Antibiotic approaches to facilitate whole cell access are well known in the conventional patch pipette prior art. Additionally, antibiotic based whole cell access is utilized in the IonWorks® HT system. However, a distinguishing feature of the PPC approach is that there may be multiple sites for antibiotic access to a cell, since a single cell would be covering multiple holes. Amphotericin approaches for conventional sized holes in a PPC device would also work.

In some embodiments, reducing the number of open holes could be achieved by increasing the density of the cells applied to each well. Typically, the number of cells in each well is about 1,000 to 200,000 cells per well. Increasing the density of cells may introduce secondary problems such as the cells sequestering test compounds applied to the well, or cells clumping and forming bridges over some of the holes preventing access of cells or beads to a hole.

In some embodiments, the spatial arrangement of the holes in each well is optimized to increase the probability of a cell reaching a hole. For example, the spatial arrangement of the holes can be optimized for the cell delivery system e.g., a circular or radial hole arrangement may be better suited to cells delivered from a vertically dispensing tip vs. a square or rectangular arrangement that might be better suited to a laminar flow cell delivery system.

In some embodiments, the substrate may be designed to enhance the likelihood that there would be a maximum of one hole per cell. This could be accomplished, for example, by spacing the holes approximately 20 µm or more apart. At 20 µm spacing, there would be 2,500 holes per square millimeter. At 50 µm spacing, there would be 400 holes per square millimeter. Optimization of the density of holes would reduce the probability of a hole being only partially blocked by only a portion of a cell.

In some embodiments, an electric field (AC and/or DC) could be used to attract the blocking particles. The particles could be drawn with greater force at an angle to the vertical to holes that are near the periphery of a cell but partly occluded by the cell. For this to work, the particles may need to carry a mobile charge on the surface or within the particle. If electrical attraction is used to bring beads to the unoccupied holes, a suitable driving voltage would be an intracellular-negative (hyperpolarizing) voltage of about 100 mV. The cells on the occupied holes should tolerate this without deterioration whether they have intact or ruptured patches. Exemplary approaches are described in the above-mentioned '815, the entire content of which is incorporated herein by reference.

Potential Advantages of the Present Invention

1. No Redundancy, Higher Throughput

The PPC system may have better, potentially four (or more) times better, throughput than an existing IonWorks® HT system because the current need for fourfold (or more) redundancy will be eliminated. Because there may be tens, hundreds, or thousands of holes in each well, a substantial number of cells are likely to be successfully whole cell clamped that express a response, thereby contributing to the aggregate current. The rate of successfully obtaining a data point from the well is very high, 95%, 99% or more. Thus, there is little need to redundantly distribute the test compound to two or more wells to be sure of measuring a response. As a result, nearly the same number of compounds can be tested as there are wells. For example, in a single cell per well add and read system with fourfold redundancy and 384 wells in each measurement plate, a maximum of 96 compounds can be tested per plate. In contrast, in a many cells per well add-and-read PPC system with no redundancy and 384 wells per measurement plate, a maximum of 384 compounds can be tested per plate. Thus, all other things being equal, the latter system will have close to four times the throughput as measured in data points per eight hour day.

2. Reduced Cost

The reduction or elimination of redundancy may dramatically reduce the cost, particularly if the cost of the measurement plate is the dominant expense. In the example above, ignoring other small contributions to the cost of running the assay and assuming that the cost of the PPC measurement plate is the same as the cost of the single-aperture measurement plate the cost per compound will be reduced fourfold. If the cost of the PPC measurement plate is twice the cost of the single-aperture measurement plate the cost per compound will be reduced by half.

3. Improved Consistency

The coefficients of variation in the PPC system are much lower than in the single-aperture system, be it an IonWorks HT or another single-aperture system. This sometimes allows you to obtain a concentration response curve from a single set of measurements whereas in other systems it might be necessary to repeat the concentration response curve several times to achieve statistical robustness.

4. Ability to Assay Ligand Gated Ion Currents

The PPC approach of using multiple cells per well may enable a simple add-and-read system to work with LGICs for the same reason that fluorescence plate readers (such as the FLIPR® plate reader from Molecular Devices Corporation) can do so. When there are a large number of cells from which measurements are made in each well, the ensemble average of all the measurements is much less variable than the individual expression levels. Thus, it is possible to measure the control response in one or a small number of wells and use this as the reference level (i.e., 100%) for the test compound responses measured in each of the remaining wells. The errors in this approach reduce as the number of cells per well increase.

5. Higher Performance than Fluorescence Based Approaches

This PPC may be better than existing fluorescence microscopy based approaches used to assay ion channel function, such as the FLIPR® plate reader, because direct recording of ion channel current has much higher temporal resolution and allows direct voltage control of the cell or membrane being tested.

The PPC systems described below, including apparatus and methods, and components and/or steps thereof, may be used alone and/or in conjunction with the systems (including apparatus and methods, and components and/or steps thereof) described above and in the above-mentioned '684 and '815 applications, the entire contents of which are incorporated herein by this reference.

Estimation Of Electrophysiological Parameters

The present invention also provides systems, including apparatus and methods, for estimating electrophysiological parameters, particularly when compensation of one or more of these parameters has been enabled. These systems may involve using values of a parameter of interest determined with a reduced or eliminated compensation to adjust or correct values of the parameter determined with the compensation enabled. For example, in some embodiments, this may be achieved by recording a current response to a square voltage pulse with whole-cell compensation disabled in the amplifier, then adding this stored current response to any subsequent current response that has been recorded with whole-cell compensation enabled. The summed current response then may be analyzed to estimate various electrophysiological parameters.

More generally, the approach may be employed using any suitable pulse profile (e.g., square, triangular, sinusoidal, etc.) and any suitable pulse parameter (e.g., voltage, current, etc.), depending on the nature of the experimental system, the data being sought, and so on.

Figure 10:
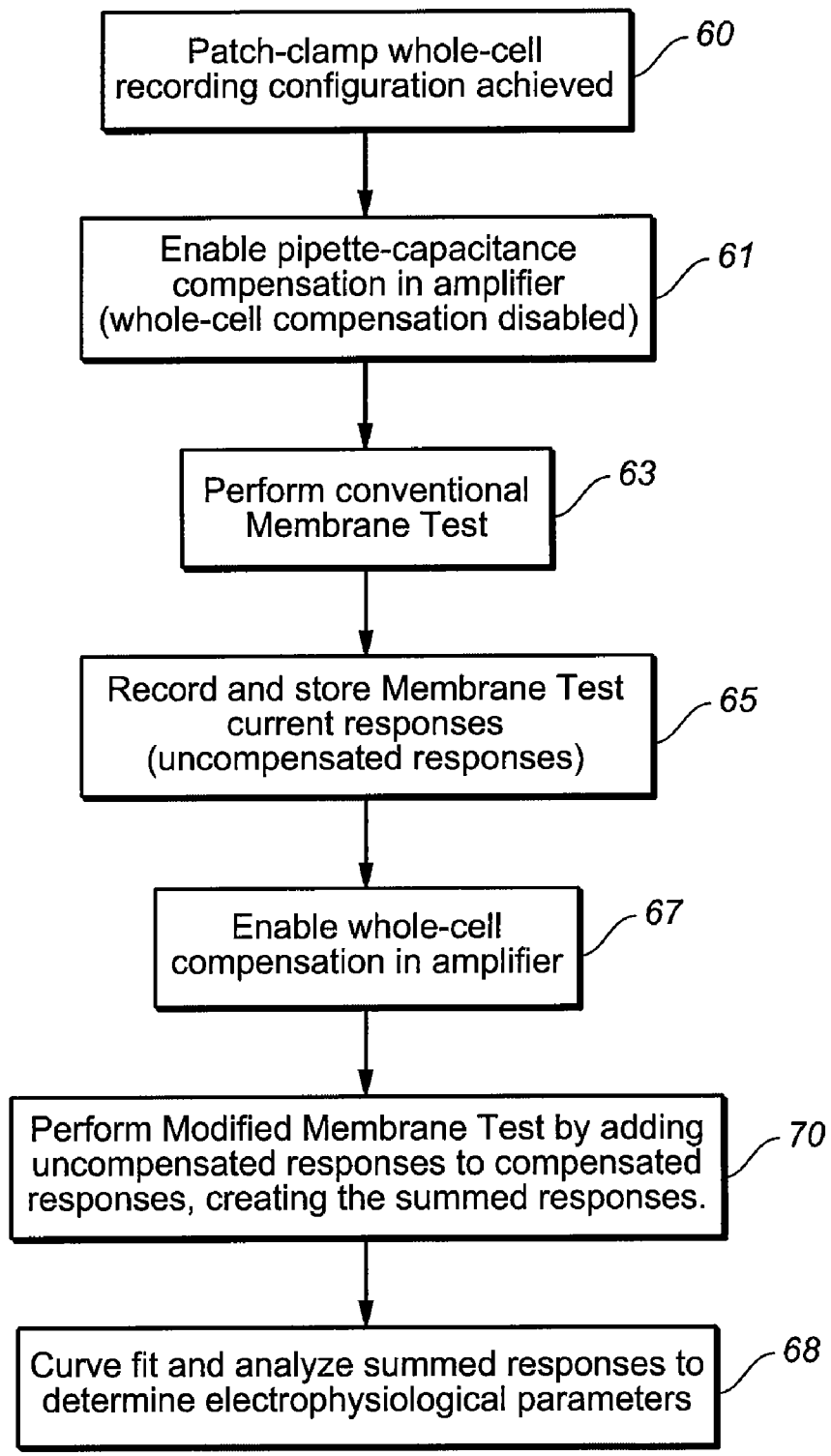
FIG. 10 is a flowchart showing a modified membrane test, in accordance with aspects of the present invention.

For example, FIG. 10 shows an exemplary embodiment of the present invention. First, a patch clamp whole-cell recording configuration is achieved (step 60). Then pipette-capacitance compensation in the amplifier is enabled and the whole-cell compensation is disabled (step 61). In this embodiment, at the onset of an experiment, prior to enabling amplifier compensation of whole-cell capacitance, access resistance, or leak resistance, the current response to a square voltage pulse, the "membrane test pulse," of a cell under voltage clamp control is recorded and stored (step 63). In some cases, it may be preferable to record and store a series of responses to the membrane test pulses (step 65). These are the uncompensated membrane test current responses. The whole-cell compensation of the amplifier then is enabled (step 67). Next, further current responses of the cell to membrane test pulses are recorded. These are the compensated membrane test current responses. Immediately after the compensation in the amplifier is enabled, the compensated membrane test current responses are negligible, but as the experiment proceeds, the membrane capacitance, the access resistance, and/or the leak resistance may change, resulting in a small but difficult to measure signal. To enable the measurement, prior to the analysis of the compensated membrane test currents, the uncompensated membrane test pulse currents are added to the compensated membrane test currents to create the summed membrane test currents. The signals in the summed membrane test currents typically are well above the noise of the system. The summed membrane test currents then are analyzed, for example, using conventional curve fitting routines, to estimate various electrophysiological parameters, for example, the series resistance (step 68). This summation of the current responses prior to subsequent analysis is denoted as a modified membrane test (step 70). In some embodiments, to reduce noise, multiple uncompensated membrane test currents are averaged prior to summation with the compensated membrane test currents. For faster measurements, fewer uncompensated membrane test currents can be used, because fewer pulses inherently take less time for acquisition.

The present invention may provide one or more advantages over prior systems. First, the present teachings may allow the use of independent amplifier and digitizers and may not require any control of the amplifier to perform the whole cell measurement. Existing technology requires (i) a tight coupling between the amplifier and the digitizer to allow compensation in the amplifier to be deactivated at precise times for a precise duration during the acquisition, so that the membrane parameters can be measured, or (ii) a long time between stimulation sweeps during an experimental manipulation to allow sufficient time for a loosely coupled amplifier to respond to the commands to deactivate and activate compensation (time would need to be allocated twice between each sweep; one time to disable the compensation, then measure the whole cell parameters, and a second time to enable the compensation before the next sweep), or (iii) a software based lock-in amplifier that applies a sinusoidal stimulus and measures the phase and amplitude of the response. Second, the present teachings also may adjust for the actual effect of the combined digitizer and amplifier, not just the theoretical effect of the amplifier. Third, the present teachings may be cost-effective and usable on existing hardware in the field, without expensive upgrades to additional hardware.

Accurate determination of membrane parameters in software may require a wide recording bandwidth, for example, 5 kHz or greater for mammalian cells in a patch clamp configuration. Once an experiment begins, the bandwidth of the membrane current often is low-pass filtered before digitization to bandwidths that are too low for accurate software determination of the membrane parameters. Unless the amplifier and the digitizer were tightly coupled, the time taken to increase the bandwidth before determining the membrane parameters then increase it again to continue the acquisition of the experimental data would make the system inefficient. Therefore, in some embodiments of the present teachings, a software filter may be used after the digitizer to control bandwidth, thereby allowing for the necessary precise and rapid manipulation of the bandwidth for acquisition of accurate membrane test current responses.

Figure 11:
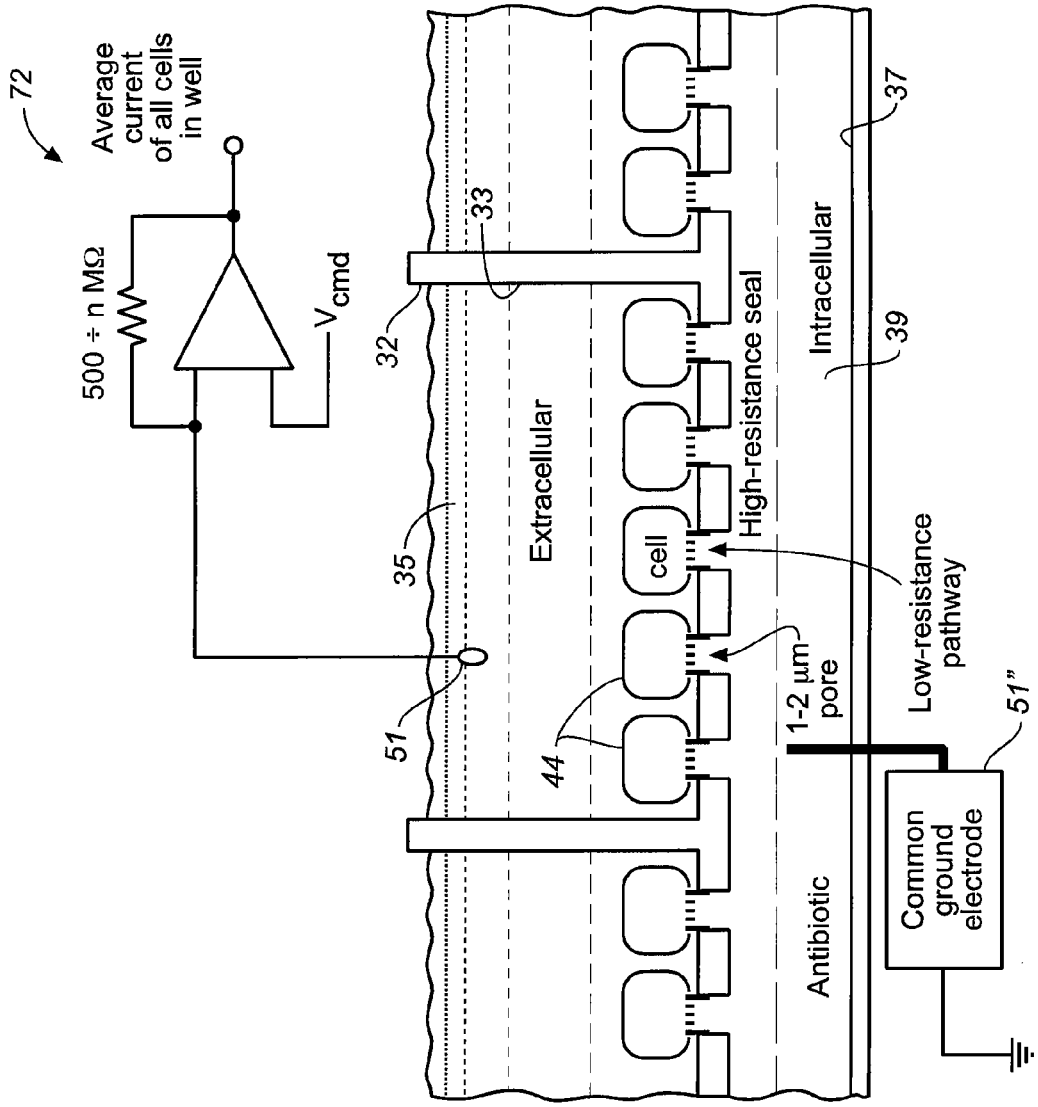
FIG. 11 is a schematic cross-sectional view of another exemplary PPC device in accordance with the present invention.

Improved Data Consistency And Success Rates in the Measurement of Ionic Currents In the parallel patch clamp of the present invention, a single voltage-clamp amplifier sums the whole-cell currents from multiple cells at once, each sealed to a separate hole in a planar substrate well (see, e.g., FIG. 11). The currents from all the cells are aggregated into the same amplifier. An average on a per cell basis is formed either by reducing the gain of the voltage clamp amplifier compared to the gain that would be used to record from a single cell or by subsequently dividing the measured signal in electronics or software. The average current exhibits reduced noise and improved consistency compared with the currents measured from single-aperture systems.

In this embodiment, the PPC technique is identical to those discussed above in which multiple cells 44 are voltage clamped within an individual well and all their currents measured simultaneously (i.e., their aggregate current) by a single voltage-clamp amplifier 72. An individual well 32 is shown within a multi-aperture substrate, which well has an "n" number of apertures. The common intracellular chamber 37 is shown with the ground electrode 51" as well as the voltage clamp amplifier connected to the electrode for the upper well of the microplate.

The resulting ensemble currents are more consistent from well to well and the success rate for each recording attempt may be greater than 95%, 99% or more. This increased data consistency and likelihood of a successful recording, combined with parallel measurements, allows the direct electrophysiological recording of thousands of ensemble ionic currents per day. Therapeutic groups in drug discovery programs require this order of throughput to screen directed compound libraries against ion channel targets related to diseases of excitable cells, such as neurological and cardiac disorders, or nervous system maladies such as pain. The potential for studying the function of large numbers of ion channel mutants may be realized with the technique. The procedure incorporates subtraction methods that correct for expected distortions and reliably produces data that agree with previous patch clamp studies.

Present whole-cell patch clamp methodology has only moderate consistency and throughput, rendering impractical functional measurements on large numbers of ion channel ligands or on large numbers of unknown or mutant channel genes. Voltage clamp techniques developed over 50 years ago allowed the control of the membrane voltage and measurement of voltage-dependent ionic currents for the first time in large molluscan and amphibian neurons. The patch clamp technique, described in detail in 1981, is a refinement of voltage clamp techniques that allows the measurement of currents in much smaller cells, including mammalian cells (see, e.g., Hamill et al., *Improved patch clamp techniques for high-resolution current recording from cells and cell-free membrane patches*, Pflugers Arch 391, 85-100, 1981). Patch clamp assays face a number of challenges, including modest success rates for each patch clamped cell and the variability in cell-to-cell expression levels. Even in stably transfected cell lines, the measurable expression levels can vary tenfold (see, e.g., Trapani et al., *Control of ion channel expression for patch clamp recordings using an inducible expression system in mammalian cell lines*, BMC Neurosci 4, 15, 2003). These factors combine to force low throughput with conventional patch clamping of a single cell, vitiating a) functional measurements on large numbers of compounds for studying the mode of drug binding or for drug discovery and (b) experiments on large numbers of unknown or mutant channel genes. Because of this, ion channels are a viable but under-represented target class for drug discovery, whether in academic or pharmaceutical company contexts. In attempts to increase the throughput of patch clamping, automation was initially introduced by utilizing robotics designed to mimic the human researcher or by positioning suspended cells at the surface of a drop of solution and approaching the cells with the recording electrode, but neither of these systems provided a substantial increase in throughput or data quality (see, e.g., Xu et al., *Ion-channel assay technologies: quo vadis?*, Drug Discov Today 6, 1278-1287, 2001). A significant advance toward increased throughput was achieved when the pipette was replaced by a substrate containing an array of apertures, each 1-2 μm in diameter (see, e.g., Fertig et al., *Microstructured glass chip for ion-channel electrophysiology*, Phys Rev E Stat Nonlin Soft Matter Phys 64, 040901, 2001; Klemic et al., *Micromolded PDMS planar electrode allows patch clamp electrical recordings from cells*, Biosens Bioelectron 17, 597-604, 2002; Pantoja et al., *Bilayer reconstitution of voltage-dependent ion channels using a microfabricated silicon chip*, Biophys J 81, 2389-2394, 2001; Schmidt et al., *A chip-based biosensor for the functional analysis of single ion channels*, Agnew Chem Int Ed 39, 3137-3140, 2000; and Schroeder et al., *IonWorks™ HT: A New High-Throughput Electrophysiology Measurement Platform*, J Biomol Screen 8, 50-64, 2003). Such automated systems have enabled a substantial increase in throughput and direct electrophysiological screening (see, e.g., Kiss et al., *High throughput ion-channel pharmacology: planar-array-based voltage clamp*, Assay and Drug Development Technologies 1, 127-135, 2003), but they have not changed the standard paradigm of one-cell per measurement nor have they led to an improvement in data consistency. Success rates using planar patch techniques have been reported to range between 30-80% for obtaining a data point from an individual cell (see e.g., Fertig et al., *Whole cell patch clamp recording performed on a planar glass chip*, Biophys J 82, 3056-3062, 2002; Kiss et al., 2003; Schroeder et al., 2003).

In accordance with the present invention, data consistency and success rates is improved by measuring the average response of many cells in parallel using the parallel patch clamp (PPC) technique. Such a change in the measurement paradigm is an extension of the whole-cell patch clamp itself. In whole-cell patch clamp, the measured current is the ensemble average of thousands of single-channel currents contributed by the individual ion channels distributed in the membrane (see, e.g., Anderson and Stevens, *Voltage clamp analysis of acetylcholine produced end-plate current fluctuations at frog neuromuscular junction*, J Physiol 235, 655-691, 1973). The PPC technique makes a total measurement of the ensemble currents in cells sealed to an array of measurement apertures (up to one cell per aperture) in each well of a microplate using a single voltage clamp amplifier per well. Ideally, the measured current is the average of all of the ensemble currents from each the voltage-clamped cells in one well, but in practice it also contains confounding currents from apertures that did not successfully form a seal with a cell, or from non-expressing cells. Leak-subtraction techniques are used to identify and remove the confounding currents and small residual effects of these currents are outweighed by the improvements achieved in data consistency and success rates using the PPC technique. The increase in data consistency that the PPC technique provides allows success rates for experimental runs utilizing 384 well microplates to exceed 95% or 99%, and frequently runs are 100% successful.

The use of the PPC technique on three types of ion channels exogenously expressed in stable cell lines will be discussed: $K_v1.3$ and human ether-a-go-go-related gene (HERG) channels in Chinese hamster ovary (CHO) cells and $Na_v1.5$ channels in Chinese hamster lung (CHL) cells. A schematic of a single well and two adjacent wells in the microplate is shown in FIG. 11. Cells are added to the well and vacuum is applied to the lower common chamber. Note that unlike single aperture patch clamp, the PPC approach utilizes wells having multiple apertures per well.

Figure 12A:
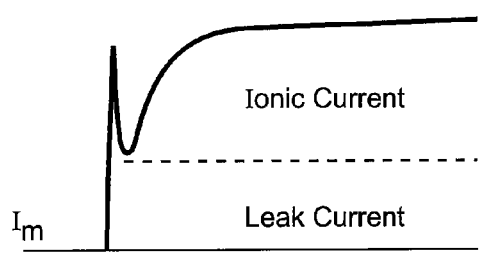
FIG. 12A and FIG. 12B are graphs illustrating ionic and leak currents before and after passive leak current has been subtracted, respectively.
Figure 12C:
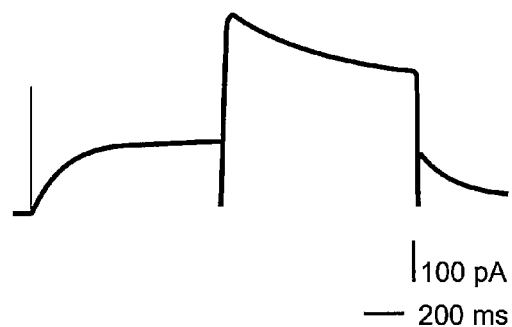
FIG. 12C and FIG. 12D are graphs illustrating channel current measured using the PPC technique of the present invention and using a single aperture technique, respectively.
Figure 12B:
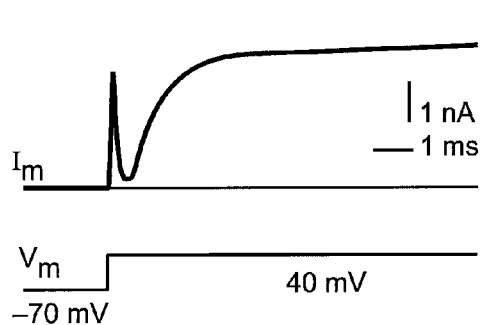

FIG. 12A and FIG. 12B show a typical recording of $K_v1.3$ currents before and after passive leak subtraction. The PPC approach normalizes the aggregate of ensemble currents of each well in all figures to a single aperture equivalent current by dividing the population total current by 64 (the number of apertures within the well).

FIG. 12A illustrates unsubtracted Kv1.3 ionic and leak currents measured with a single amplifier per well. Activation of the voltage-dependent current is seen after the decay of the capacitive transient, the ionic current is separated from the leak current by the dashed line. The dotted line is the baseline current at the holding potential. At the time of the voltage step, the membrane capacitive transient current is seen followed by the characteristic slower activating ionic-current response of the $K_v1.3$ channel. Leakage current through the seal is the time-independent current seen in the unsubtracted sweep of FIG. 12A. The dashed line separates the time-dependent $K_v1.3$ currents (above the dashed line) from the pedestal leak current. A key to the success of the PPC technique is the fact that the leakage current is linear (ohmic) while the voltage-dependent ionic current is non-linear with respect to voltage. The leakage current is comprised of two major components: the current around successfully patched cells and the current through apertures that are either open or partially occluded by debris.

Resistive leak subtraction techniques are applied to digitally subtract the calculated leak current at any voltage estimated from the response to a small hyperpolarizing test voltage step applied prior to test voltage steps. In the event the leakage current changes slowly with time due to changes in the electrical seal, errors are minimized by implementing the leak subtraction process at the start of each sweep. After subtraction of the leak current, the remaining current exhibits the characteristic activation time course of the $K_v1.3$ current recorded by conventional patch clamp (see, e.g., Chandy et al., *A family of three mouse potassium channel genes with intronless coding regions*, Science 247, 973-975, 1990). The voltage-dependent current after passive leak current has been subtracted is illustrated in FIG. 12B.

Figure 12D:
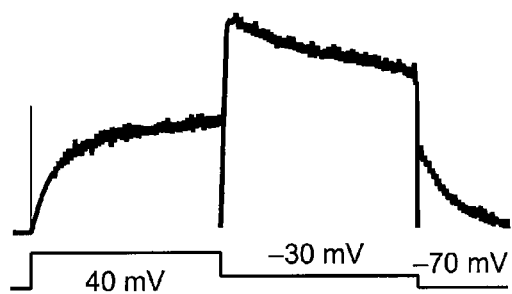

The ensemble averaging that is inherent to the PPC technique improves the signal to noise ratio, as can be seen by comparing the PPC recording of FIG. 12C with the single aperture recording of FIG. 12D. These figures illustrate human ether-a-go-go-related gene (HERG) potassium channel current measured using the PPC (FIG. 12C) and the single aperture technique (FIG. 12D). Note the greater signal to noise ratio in the PPC trace (FIG. 12C). It should be noted that in FIG. 12A, FIG. 12B, and FIG. 12C, the displayed current is the measured current divided by 64 to allow currents to be represented as the average current per aperture in the chamber, FIG. 12D is the measured current through a single aperture. The improved signal to noise ratio allows the measurement of small currents that cannot be resolved in prior single aperture modes.

FIG. 13 illustrates the improved data consistency of the PPC technique. Each 384 well plate is measured in eight of these groups. PPC current scale is the mean current per aperture (i.e. total measured current/64), single aperture current scale is as measured.

Typical current recordings from eight adjacent wells measured using the single aperture (FIG. 13A) and PPC (FIG. 13B) modes of recording are shown, namely $Na_v$ 1.5 currents measured with the single aperture and PPC technique in 384 well microplates. Sample rates were 10 kHz with a signal bandwidth of 3 kHz, dashed lines indicate 0.61 ms after pulse onset.

FIG. 13A illustrates single aperture recordings from adjacent wells (A1-A8) are shown. The mean current magnitude for this experimental run was 3.6±1.4 nA (mean±SD, n=285), and time to peak current was 0.76±0.15 (mean±SD, n=285 wells, range 0.5-1.4 ms). FIG. 13B illustrates PPC recordings from adjacent wells (A1-A8) are shown. The magnitude and kinetics of PPC measured Na inward currents are more consistent across the plate. The mean current amplitude was 1.9±0.3 (mean±SD, n=375 wells), and time to peak current was 0.61±0.06 ms (mean±SD, n=375, range 0.5 to 0.8 ms). The current amplitudes and time to peak for the PPC currents is much more consistent than the single aperture recordings.

Figure 13C:
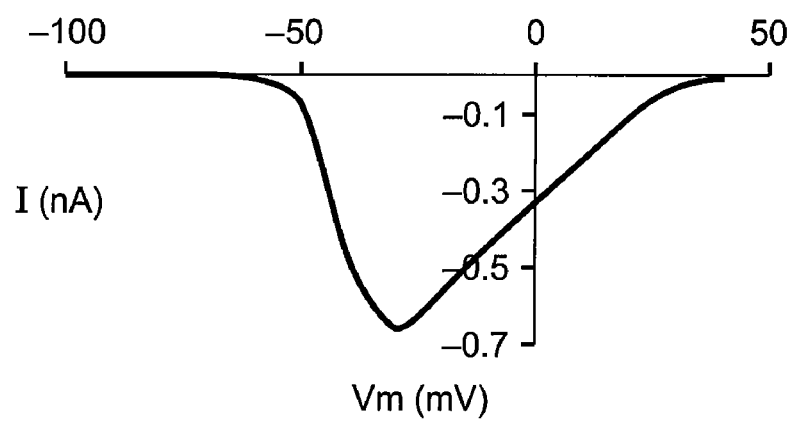
FIG. 13C is a graph illustrating an I-V curve measured in a single PPC system well.
Figure 13D:
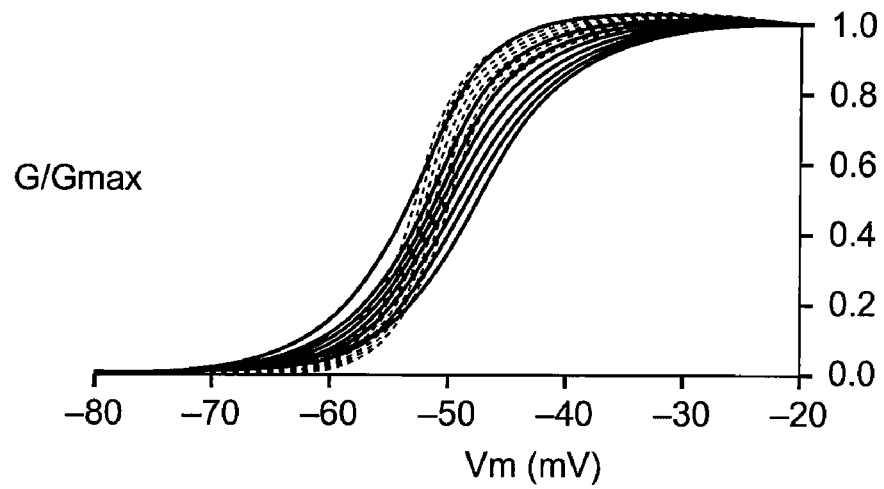
FIG. 13D is a graph illustrating G-V curves measured from a family of reads from a single group of 48 wells.

FIG. 13C shows the current-voltage (I-V) curve from a single PPC well, the curve is very similar to that obtained using conventional patch clamp except that the voltage for the peak current is left shifted by 10-20 mV from published values (see, e.g., Chahine et al., *Electrophysiological characteristics of cloned skeletal and cardiac muscle sodium channels*, Am J Physiol 271, H498-506, 1996; Nuss et al., *Cardiac sodium channels (hH1) are intrinsically more sensitive to block by lidocaine than are skeletal muscle (mu 1) channels*, J Gen Physiol 106, 1193-1209, 1995) due to the voltage drop of 10-20 mV across the cell access resistance (~10 Mohm) and aperture resistance (~3 Mohm). Conductance-voltage (G-V) curves (FIG. 13D) obtained from a single group of 48 wells illustrate the data consistency of the technique. FIG. 13D illustrates Boltzmann fits to activation (G-V) curves measured from a family of reads from a single group of 48 wells. The V(0.5) for this group of recordings was −44±0.6 mV (mean±SD, r=0.996) similar to values reported in the literature (see, e.g., *Sheets and Hanck, Gating of skeletal and cardiac muscle sodium channels in mammalian cells*, J Physiol 514 (Pt 2), 425-436, 1999).

When using a single aperture substrate, the acceptable seal resistance has been shown to be in the range of 50-300 Mohm, averaging ~120 Mohm (see, e.g., Kiss et al., 2003; Schroeder et al., 2003). For the same cell line, using the 64 aperture substrate, the average seal resistance in each chamber normalized to a per-aperture value is usually lower for a successful experimental run, averaging 50 to 110 Mohm. Ionic currents and pharmacological results are as expected when the normalized seal resistance is above 50 Mohm (e.g., when the seal resistance is approximately 42% of the average acceptable seal resistance); when the average seal resistance is below ~30 Mohm the technique generally fails. It is believed this is due to poor cell quality and is an uncommon occurrence (<2% of runs). For successful runs there is no way to directly determine the percentage of apertures that remain open or partially occluded by debris, however to estimate our observed range of seal resistances (50 to 110 Mohm) the present invention has two models (see, e.g., FIG. 17 illustrating prediction of percentage of open apertures assuming leak for properly clamped cell is 120 Mohm and all other apertures are partially occluded at 10 Mohm or completely open at 3 Mohm). The first is that up to 12% of the apertures (7 of 64) were partially occluded at the 10 Mohm level and the second is that up to 3% of the apertures (2 of 64) were completely open at 3 Mohm. Therefore, for an individual run to be successful there must be a high percentage of seals. After the cells are optimized and a sufficient density of cells is added to each well, the aforementioned seal rate is not difficult to achieve.

Figure 14A:
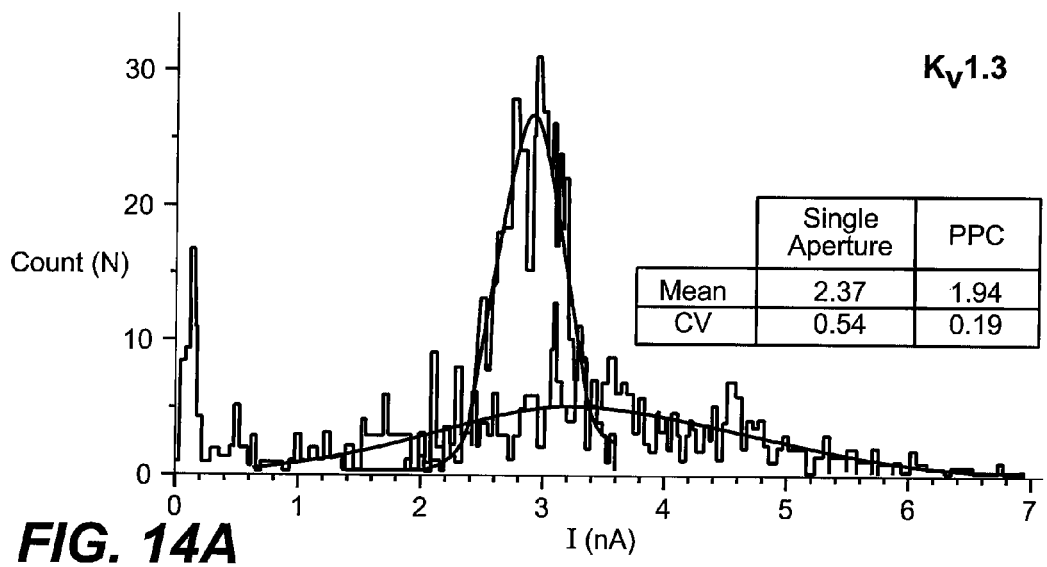
FIG. 14A, FIG. 14B, and FIG. 14C are current amplitude histograms for individual wells using a single aperture versus a 64 aperture PPC substrate.
Figure 14B:
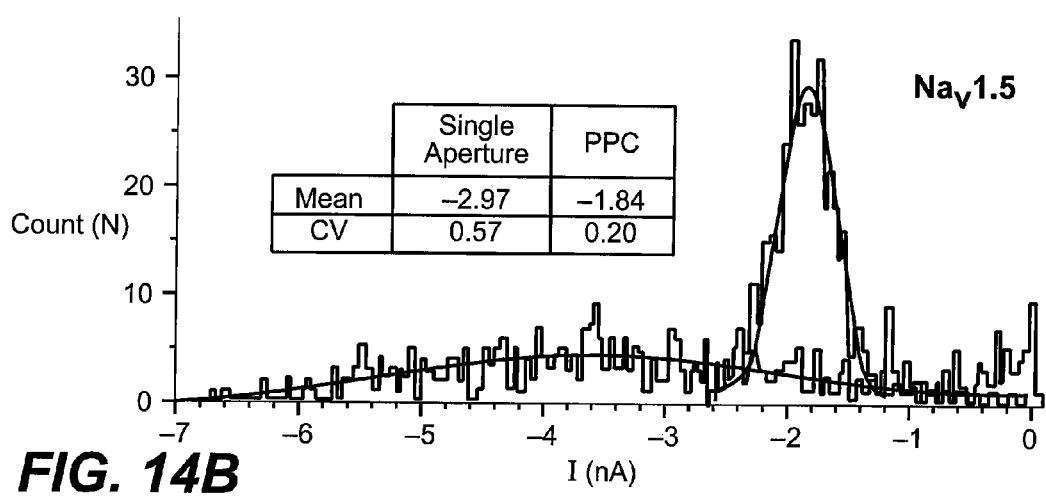
Figure 14C:
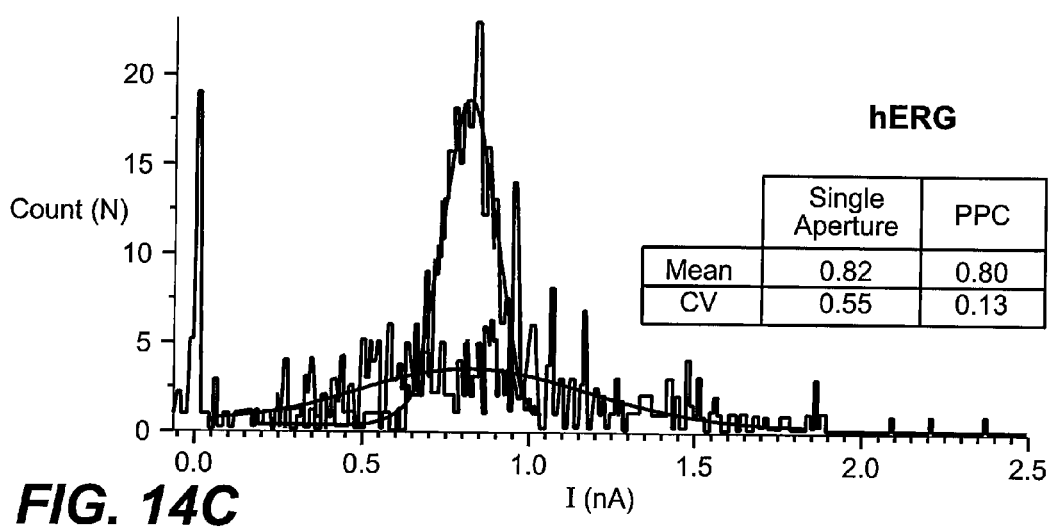

Typical individual well current amplitude histograms are shown in FIG. 14, each plot showing current amplitude histograms for individual wells using a single aperture versus 64 aperture (PPC) substrate (e.g., superimposed). Each run was recorded with cells from the same culture passage on the same day and a run consists of the measurement of 384 wells from a single microplate. Current amplitude histograms for $K_v1.3$ (A), $Na_v1.5$ (B), and HERG (C) channels are shown.

The current amplitude distribution for single aperture runs is broad, illustrating the biological variability of conventional planar patch clamp measurements from single cells. As expected from the ensemble averaging procedure of the PPC technique, it produces a tighter distribution of current amplitudes. The PPC histograms have a narrower distribution when compared to histograms constructed from single aperture single cell recordings. The coefficient of variation (CV) is 2-4 fold smaller on the PPC histograms. Non-expressing cells comprise the distribution of cells on the single aperture histograms near zero current magnitude. The single aperture Gaussian fits exclude the non-expressing cells, while all summary statistics include all cells including the non-expressing cells. The non-expressing cells do not contribute a separate peak near zero current; instead they form part of the average PPC current amplitudes, so that the mean current amplitudes for the PPC runs are less than those for successful single aperture measurements.

The advantage of the PPC technique over conventional or single aperture planar patch clamp is the reduction of measurement variability resulting from expression variability and a substantial increase in the success rate of obtaining a data point from each attempted measurement. It is important to define success rate so that a comparison can be made between PPC and single aperture substrates. Success rate is defined as the percentage of ionic current recordings obtained from a 384 well plate. A well can fail for any of the following four reasons; 1) the well can be unusable because the apertures are blocked by debris or a bubble, 2) the cells can fail to form a usable seal >50 Mohm, 3) the overall current can be too small due to a lack of expression, 4) the current amplitude can be unstable over time (±>20% over five minutes). The graph in FIG. 15 shows the success rates of PPC and single aperture individual runs for $K_v1.3$, $Na_v1.5$, and hERG. The bar graphs show a 99.3% rate (n=3456 wells) for $K_v1.3$ channels in PPC mode compared to 80.1% (n=4608 wells) for the single aperture mode. The success rate for $Na_v1.5$ channels in PPC mode was 95.5% (n=3072 wells) and 71.3% (n=3456 wells) in single aperture mode. HERG channels had success rates of 97.3% for PPC mode (n=1536 wells) and 61.0% for single-aperture mode (n=3072 wells). Experimental runs are shown that were designed specifically to measure current stability, whereby saline (mock compound) is added instead of compound containing solution across the entire microplate.

As shown in FIG. 15, the PPC technique is very predictable with optimized cells. Since optimizing the $K_v1.3$, $Na_v1.5$, and HERG cell lines, more than 100 consecutive runs have been conducted where the PPC success rates were 95-100%.

Figure 16A:
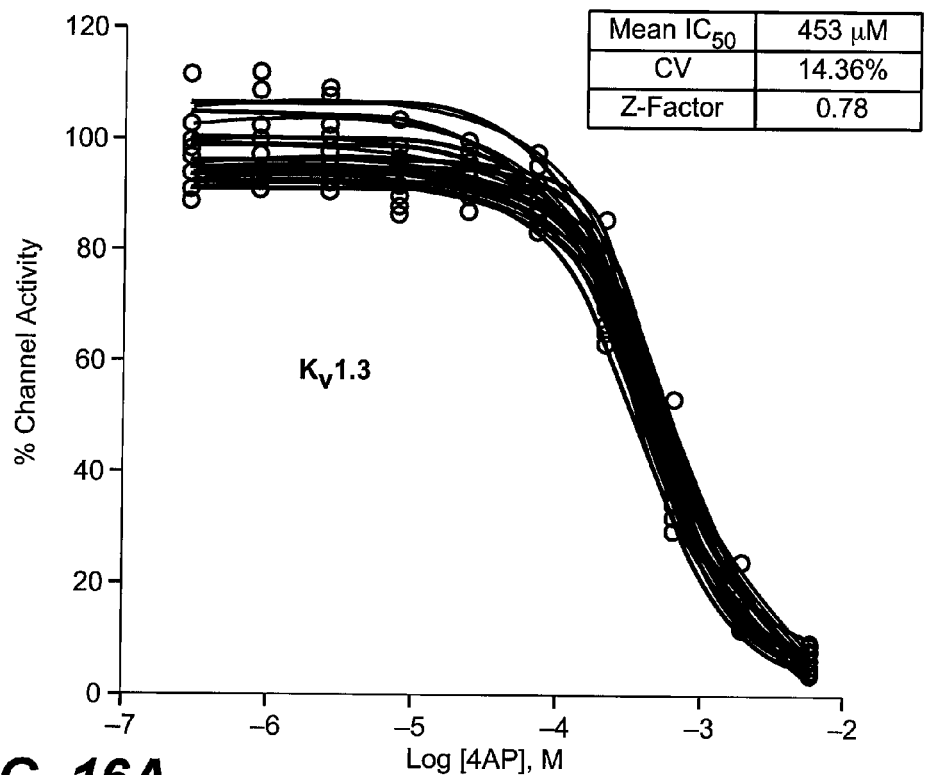
FIG. 16A and FIG. 16B are graphs illustrating pharmacology of $K_v1.3$ and $Na_v1.5$ channels.
Figure 16B:
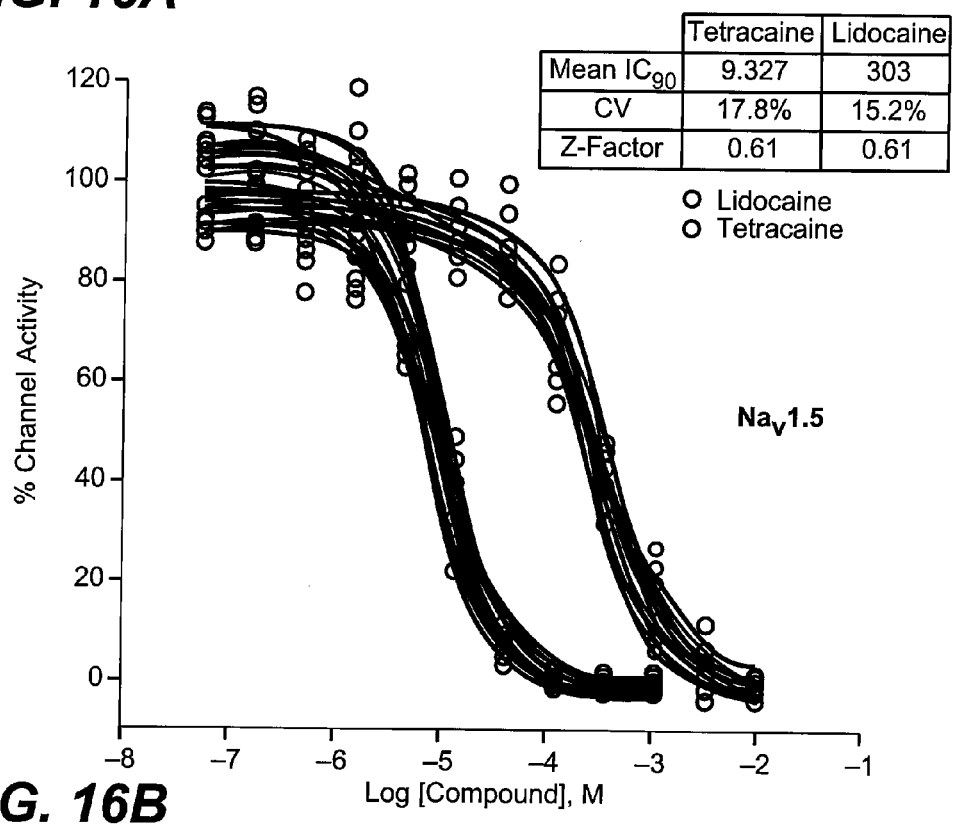

PPC ensemble averaging reduces the biological variability, allowing for more consistent pharmacological results when testing compounds against ion channel targets. Thirty-two ten-point IC50 plots for 4-aminopyridine are plotted in FIG. 16A and were obtained using the PPC technique in a single run (66 minutes). Sixteen IC50 curves each for tetracaine and lidocaine were obtained in 70 minutes and are plotted in FIG. 16B.

The direct measurement of ion channel currents in drug discovery settings has been limited to the measurement of individual cells using conventional pipette or single aperture planar patch clamp. The problems associated with these techniques are that many data points are lost due to data inconsistencies caused by the variability in channel expression levels, or failed measurement attempts caused by technical problems including low seal resistances or failure to obtain the whole cell-recording mode. Drug discovery programs need the capability to screen tens of thousands of compounds over a period of a few weeks with a low percentage of lost compounds so that a retesting of large numbers of compounds is not required. The PPC technique resolves many of these issues including data inconsistencies caused by a lack of channel expression and data points lost due to low seals. Ensemble averaging of the currents from 64 cells results in data points rarely being lost due to non-expressing cells. The key to this success is that it does not matter that a small percentage of the patch clamped cells in each well do not express exogenous currents; what matters is that a substantial number of them do indeed express currents of interest and that these currents contribute to the measured ensemble average current. All small endogenous currents present in non-expressing cells are overwhelmed by the overall expressed current and essentially averaged out of the final current signal. Poor seals that occur in the planar patch single aperture mode are indeed present in the PPC mode as well, these relatively small linear currents are averaged into the larger total measured total current and then subtracted out to give the large non-linear ensemble currents of interest.

The consistency of the PPC technique is a clear advantage in compound screening because it makes it unnecessary to make repeated compound applications in order to be confident of screening the majority of compounds in the library. The consistency is also an advantage for detailed studies on the pharmacology of individual compounds. For example, because of the inherent consistency in the PPC method it is possible to obtain ten-point dose response curves from ten wells, obviating the need to average many responses from many wells at each concentration in order to reduce the variability at each concentration to an acceptable level.

The screening of large numbers of mutant channels can also be envisioned using the PPC technique in both academic and drug discovery settings. Clonal selection is already routinely performed using single aperture planar patch clamp format whereby 12 individual clones of the same channel are tested with an n of 32 for each clone in a 384 well run lasting less than one hour (Guthrie et al., *A Place for High Throughput Electrophysiology in Cardiac Safety: Screening hERG Cell Lines and Novel Compounds with the IonWorks HT™ System*, Journal of Biomolecular Screening *In Press*, 2005). Because of the consistency of PPC currents, kinetic studies could be carried out on transiently transfected ion channel mutants, with up to 48 different mutants tested in a one-hour run, with an n of 8 PPC wells per mutant. An n of 8 PPC wells should be sufficient to reliably detect subtle kinetic changes as the ensemble current in each well is already inherently averaged from up to 64 individual cells. Ion channel studies where potential regulatory sites (e.g. phosphorylation, calcium binding, voltage-sensing regions) have been knocked out by site directed mutagenesis could be tested, and the effect of these mutations could be examined related to current kinetics, regulation, or expression. Whole regions of the ion channel proteins could be explored or all the consensus sequences for a particular regulatory molecule could be individually mutated and scanned for effects very rapidly using PPC.

Larger scale genetic rescue screening could also be performed on non-conducting channels where a mutation has caused a loss of function. Frequently, interaction pairs between amino acid residues or a particular tertiary structure within a channel protein are required for proper channel function. A mutation scan substituting all amino acids at a particular residue can be performed in the suspected area of residue interaction or tertiary structure disruption. Since the non-conducting mutants will not contribute any current to the ensemble average, multiple mutations could be pooled and tested in a single PPC well. Multiplexing the mutant screening in this way would increase the rate of mutants screened, the degree of multiplexing at the single well level would be determined by the level of desired sensitivity of the rescue assay. Increasing the number of mutants pooled into a single well would inherently reduce the output signal from any given rescue mutant due to the averaging of signals from the other mutants. Thus, the threshold of detection of the assay could be titrated: pooling many clones into a PPC well would reduce the sensitivity but increase the rate of the screen, whereas reducing the number of clones pooled would increase the sensitivity of the assay.

Two Models to Describe the PPC Seal Resistances

Since a single parallel measurement is made in a PPC well from multiple recording sites and multiple cells, there is no way to determine what the values of the seals are in the individual branches of the parallel circuit. For this reason, two models in accordance with the present invention have been provided to help estimate the proportion of "successful" seals, partially occluded holes, and completely open holes within the parallel circuit. The first model assumes that there are only two populations of seals at the recording sites, one being successful seals (120 Mohm) and the other completely open holes (3 Mohm). As the seal rate drops from 100% the mean seal resistance for the parallel circuit drops off sharply. The measured range in seals that typically seen (50-120 Mohm) corresponds to less than 3% of the holes being completely open (or 2 of 64 holes). The second model also assumes two populations of seals at the recording sites, again the successful seals (120 Mohm), in this model, however, the other population is partially occluded holes (assumed to be 10 Mohm). With the second model, the range of observed seal resistances is obtainable only when 88% or more of the holes have seals of 120 Mohm and 12% or less (7 of 64) have partially occluded holes. The actual situation is probably something in between the two models. In other words, there is probably a mixture of successful seals, partially occluded holes, and completely open holes. In any case, both models suggest that the seal rates must be 88% or greater, once a cell line is optimized. This is not difficult to achieve on a routine basis.

The PPC is a robust technique that delivers more consistent and reproducible results than conventional whole-cell patch clamp with glass pipettes, or single aperture planar patch clamp. Consistency in each measurement is achieved by using the ensemble average of a large population of whole cell currents. The main difference between the PPC technique and recording individual whole cell currents from the equivalent number of wells is that in the PPC technique the averaging is an intrinsic process done in the analog domain. Whole cell currents from a population of cells converge in the well into a single analog amplifier, whereas in the alternative the averaging is a digital process that requires currents from individual wells to be separately acquired, then averaged. The consistency of the measurements from each well combined with the measurement of many wells simultaneously boosts the throughput of the PPC technique to a level that could never be achieved with conventional pipette or single aperture patch clamp.

Experimental Procedures

Experimental cells include: Chinese hamster lung (CHL) cells expressing $Na_v1.5$ channels; and Chinese hamster ovary (CHO) cells expressing Kv1.3 or HERG channels.

Experimental reagents and buffers include: Amphotericin (Sigma Cat. # A-4888), DMSO (Sigma Cat. # D-2650); Versene™ (Gibco Cat. #15050); Internal Buffer (in mM): 140 KCl, 2 $MgCl_2$ 5 EGTA, 10 Hepes pH to 7.2 with KOH (Sigma Cat. #'s P-9333, M-1028, E-0396, H-7523, P-5958); External Buffer (in mM): 137 NaCl, 4 KCl, 1 $MgCl_2$, 1.8 $CaCl_2$, 10 Hepes, 10 Glucose, pH to 7.4 with NaOH (Sigma Cat #'s S-7653, P-9333, M-1028, Fluka Cat. # 21115, Sigma Cat. #'s H-7523, G-7528, Fisher Cat. # SS266-1).

Experimental tissue culture flasks include: Cells grown in T-75 flasks (Corning Cat. # 430641).

Experimental cell culture media include:
a. $Na_v1.5$: Dulbecco's Modified Eagle Medium containing L-glutamine, glucose, pyroxidine HCl, without Na pyruvate (Gibco, Cat#11965-092) plus the following additives: 10% FBS (50 mls/500 ml; Irvine Scientific: Cat# 3000), 1% (5 mls.) Genetecin (Invitrogen: Cat#10131027), 1% (5 mls.), Pen/Strep (Irvine Scientific: Cat#9366);
b. $K_v1.3$: DMEM/Ham's F-12 (Sigma, Cat#D8437) plus the following additives: 10% FBS (50 mls/500 ml; Irvine Scientific: Cat# 3000), 1% (5 mls.) Genetecin (Invitrogen: Cat#10131027), 1% (5 mls.), Pen/Strep (Irvine Scientific: Cat#9366), 1% Non Essential Amino Acids (Irvine: Cat# 9304); and
c. hERG: HAMS F12 Nutrient Mixture containing GlutaMAX (Gibco, Cat#31765-035) plus the following additives: 10% FBS (50 mls/500 ml; Irvine Scientific: Cat# 3000), 1% (5 mls.) Genetecin (Invitrogen: Cat#10131027), 1% (5 mls.) Pen/Strep (Irvine Scientific: Cat#9366), 1% Non Essential Amino Acids (Irvine: Cat# 9304).

Experimental instrument and planar substrates include: IonWorks Quattro instrument (0200-6140); PatchPlate™ consumable (single aperture; 9000-0688); and PatchPlate PPC™ consumable (multi-aperture; 9000-0902), all from Molecular Devices Corporation.

Cells were cultured in T-75 flasks and passaged every two to three days at 1:3 to 1:6 dilutions. Cells were also maintained at a lower seeding density (1:50) and passaged every 3-4 days. Flasks near confluency that were seeded at the lower seeding density cells were used frequently (~every 1-2 weeks) to provide the source of cells seeded at the higher density.

The electrophysiology of one exemplary experiment run on the IonWorks Quattro will now be discussed. $K_v1.3$ currents were elicited by a voltage step from a holding potential of −70 mV to +40 mV for 300 ms, $Na_v1.5$ currents were elicited by a voltage step from a holding potential of −100 mV to −20 mV for 40 ms, hERG currents were measured with a pre-pulse to +40 mV (5 secs) followed by a step to −50 mV (4 secs) to elicit the currents. Compounds were incubated for 330-430 seconds between the pre-and post-compound reads. Resistive (scaled) leak subtraction was used whereby the passive seal conductance is calculated at two hyperpolarized values and calculated as an ohmic conductance across the entire voltage range used. The calculated leak current is then digitally subtracted from the total current for each sample point.

An antibiotic solution was prepared in which aliquots of amphotericin (5.0±0.3 mg) were pre-weighed and stored at 4° C. Prior to cell preparation, 180 μl DMSO was added to an aliquot of amphotericin. Amphotericin/DMSO solution was sonicated until soluble (~1 minute), added to a 50 ml conical tube of Internal Buffer and vortexed for ~1 minute. The solution was stored in the dark until ready for use.

Cells were prepared in which cells were grown to 70-90% confluence in a T-75 flask and removed from the incubator (37° C., 5% CO2) 1-2 days after plating. Growth media was aspirated from the culture flasks using a 2 ml aspirating pipette attached to a vacuum pump. Cells were gently rinsed with 2.5 ml Versene solution for ~10 seconds before the solution was aspirated.

The cells were again immersed in 2.5 ml Versene solution at 37° C. After 4-5 minutes, visibly rounded cells were easily dislodged from the bottom of the flask with a few brief taps on a solid surface. 20 ml of PBS was added to the flask and the resulting solution was used to wash the sides of the flask; the cell suspension was divided equally into two 15 ml conical tubes. The two 15 ml tubes were centrifuged at 800 rpm for 4 minutes. The cell supernatant was decanted, 1.5 ml of PBS was added per tube, the cell suspensions were combined, and the cells were gently triturated for 1 minute using a p200 pipettor. A 3 ml volume of cell suspension was added to the cell boat on the IonWorks Quattro instrument just prior to beginning the experimental run.

Data analysis included fitting concentration-response curves for Tetracaine, Lidocaine, and 4-Aminopyridine to a four-parameter equation:

$$\% \text{ of control} = 100 \ (1 + ([\text{drug}]/\text{IC50})^p)^{-1}, \quad \text{Eq. (a)}$$

where IC50 is the concentration of drug required to inhibit current by 50% and p is the Hill slope.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A system for high-throughput analysis of membranous samples having ion channels, the system comprising:
    at least one membranous sample;
    a multi-compartment structure including an extracellular chamber, an opposing intracellular chamber and a partition separating the extracellular and intracellular chambers, the partition having a plurality of apertures fluidly and electrically coupling the extracellular and intracellular chambers, at least one of the apertures being sealed by the at least one membranous sample having a seal resistance in a range between about 100 to about 1000 Mohms, another of the apertures being unsealed, the unsealed aperture having an aperture resistance less then the seal resistance by about two orders of magnitude;
    an electric source configured to apply a voltage and/or a current between the extracellular and intracellular chambers, wherein a portion of current travels through the unsealed aperture creating an electrical leak; and
    an electronic detector with a leak subtraction data acquisition protocol for making a measurement while the portion of current travels through the at least one unsealed aperture, whereby the electrical leak value is subtracted from a measured data.

2. The system of claim 1, wherein the membranous sample is selected from the group consisting of cells, vesicles, organelles, cell membrane fragments or synthetic membranes, which include an ion channel; and wherein the electric source comprises an amplifier or a patch clamp, and the amplifier has a dynamic range sufficient to measure an electric leak without saturation.

3. The system of claim 2, wherein a portion of the membranous sample is inside of the one aperture and a remainder of the membranous sample is outside of the one aperture of the partition and is substantially intact.

4. The system of claim 1, wherein the multi-compartment structure includes a plurality of extracellular chambers with a predetermined number of apertures and at least one opposing intracellular chamber, wherein the partition separates the extracellular chambers from the at least one intracellular chambers.

5. The system of claim 1, wherein the another of the apertures is open.

6. The system of claim 1, wherein the apertures have a diameter in the range of approximately 0.5 μm to 5 μm.

7. The system of claim 1, further comprising a current sensor configured to measure the current between the extracellular and intracellular chambers, wherein the current sensor and the electric source are respectively configured to apply and/or measure the current across the extracellular and intracellular chambers before the apertures are sealed by respective membranous samples.

8. The system of claim 1, further comprising a fluidics system for adding fluids to the extracellular chamber, wherein the fluidics system is configured to provide add, read and wash fluidics.

9. The system of claim 8, wherein the fluidics system is configured to disperse a solution of membranous samples in suspension into the extracellular chamber, wherein the at least one membranous samples is sealed to the at least one aperture within a requested time period of dispersion by the fluidics system.

10. The system of claim 1, further comprising:
    a first electrode in electrical contact with the extracellular chamber; and
    a second electrode in electrical contact with the intracellular chamber; wherein the first and second electrodes are electrically coupled with the electric source for applying the electrical voltage across the extracellular and intracellular chambers.

11. A method of high-throughput analysis of membranous samples having ion channels comprising:
    providing a system including a multi-compartment structure having an extracellular chamber, an opposing intracellular chamber and a partition separating the extracellular and intracellular chambers, the partition having a plurality of apertures fluidly and electrically coupling the extracellular and intracellular chambers, wherein the apertures for electrically sealing a membranous sample are selected from the group consisting of cells, vesicles, organelles, cell membrane fragments and synthetic membranes, which samples include an ion channel;

dispersing a plurality of membranous samples into the extracellular chamber such that the membranous samples seal at least one of the apertures, at least one membranous sample having a seal resistance at one of the apertures in a range between about 100 to about 1000 Mohms, and unsealed apertures, each unsealed aperture having an aperture resistance of about two orders of magnitude less then the seal resistance;

applying by an electric source electrical voltage and/or current between the extracellular and intracellular chambers while another of the apertures is unsealed; and detecting by an electronic detector a resulting current and/or voltage across the extracellular and intracellular chambers, wherein a portion of the current being a current leak travels though the unsealed aperture and its current leak value is subtracted according to a data acquisition protocol of the electronic detector.

12. The method of claim 11, wherein the dispersing step is accomplished by dispersing a solution of membranous samples in suspension into the extracellular chamber.

13. The method of claim 11, wherein the dispersing step is accomplished by at least two membranous samples sealing at least two respective apertures, the method further comprising the step of summing the resulting current and/or voltage based on the two sealed membranous samples.

14. The method of claim 11, wherein the dispersing step is accomplished by at least two membranous samples sealing at least two respective apertures, the method further comprising the step of averaging the resulting current and/or voltage based on the two sealed membranous samples.

15. The method of claim 11, wherein the dispersing step is accomplished by at least n membranous samples sealing n respective apertures, the method further comprising the step of summing the resulting current and/or voltage based on the n sealed membranous samples.

16. The method of claim 11, wherein the dispersing step is accomplished by at least n membranous samples sealing n respective apertures, the method further comprising the step of averaging the resulting current and/or voltage based on the n sealed membranous samples.

17. The method of claim 11, wherein the applying step further includes voltage clamping the one membranous sample.

18. The method of claim 11, wherein the applying and detecting steps are initiated before the membranous sample seals to the at least one aperture.

19. The method of claim 11, the method further comprising the step of recording the current.

20. The method of claim 19, wherein the recording step is begun within approximately 60 seconds from the dispensing step.

21. The method of claim 19, wherein the recording step is begun within approximately five minutes from the dispensing step.

22. The method of claim 11, the method further comprising the step of measuring the current and applying a leak subtraction data acquisition protocol.

* * * * *